(12) United States Patent
Oleynik

(10) Patent No.: US 7,075,428 B1
(45) Date of Patent: Jul. 11, 2006

(54) METHODOLOGY AND APPARATUS FOR THE DETECTION OF BIOLOGICAL SUBSTANCES

(75) Inventor: Vladislav A. Oleynik, Pittsboro, NC (US)

(73) Assignee: BioWarn LLC, Montgomery Village, MD (US)

( * ) Notice: Subject to any disclaimer, the term of this patent is extended or adjusted under 35 U.S.C. 154(b) by 0 days.

(21) Appl. No.: 11/206,200

(22) Filed: Aug. 18, 2005

Related U.S. Application Data

(62) Division of application No. 10/988,709, filed on Nov. 16, 2004.

(60) Provisional application No. 60/523,303, filed on Nov. 20, 2003.

(51) Int. Cl.
  *G08B 1/08* (2006.01)
  *G01N 33/53* (2006.01)

(52) U.S. Cl. ............... 340/539.26; 435/7.1; 435/287.1

(58) Field of Classification Search ............ 340/539.26
  See application file for complete search history.

(56) References Cited

U.S. PATENT DOCUMENTS

| | | | |
|---|---|---|---|
| 5,063,164 A | 11/1991 | Goldstein | |
| 5,151,110 A | 9/1992 | Bein et al. | |
| 5,328,847 A | 7/1994 | Case et al. | |
| 5,374,563 A | 12/1994 | Maule | |
| 5,532,493 A | 7/1996 | Hale et al. | |
| 5,632,957 A | 5/1997 | Heller et al. | |
| 5,744,902 A | 4/1998 | Vig | |
| 5,807,758 A | 9/1998 | Lee et al. | |
| 5,874,046 A | 2/1999 | Megerle | |
| 6,030,781 A | 2/2000 | Shieh | |
| 6,096,497 A | 8/2000 | Bauer | |
| 6,228,657 B1 | 5/2001 | Genovese et al. | |
| 6,322,963 B1 | 11/2001 | Bauer | |
| 6,391,624 B1 | 5/2002 | Megerle | |
| 6,432,723 B1 | 8/2002 | Plaxco et al. | |
| 6,448,064 B1 | 9/2002 | Vo-Dinh et al. | |
| 6,482,639 B1 | 11/2002 | Snow et al. | |
| 6,483,125 B1 | 11/2002 | Brousseau, III | |
| 6,548,311 B1 | 4/2003 | Knoll | |
| 6,569,384 B1 | 5/2003 | Greenbaum et al. | |
| 6,598,459 B1 | 7/2003 | Fu | |
| 6,633,240 B1 * | 10/2003 | Sweatt | 340/539.26 |
| 6,649,417 B1 | 11/2003 | Greenbaum et al. | |
| 6,653,653 B1 | 11/2003 | Brousseau, III | |
| 6,694,799 B1 | 2/2004 | Small | |

(Continued)

*Primary Examiner*—Daniel Wu
*Assistant Examiner*—Eric Blount
(74) *Attorney, Agent, or Firm*—Taylor Russell & Russell, P.C

(57) ABSTRACT

A methodology and an apparatus for the detection of biological substances employing the integration of multiple functions and units designed into and implemented in the form of an individual silicon chip, described as a sensor unit. The deployment of a set of sensor units as a group results in a distributed detecting, discriminating, and alerting network. Distribution of the sensor units facilitates the on-the-spot detection of different biological substances such as viruses, bacteria, spores, allergens, and other toxins that can be suspended in multiple media (air, liquid, blood, etc.). Besides detection/sensing, the individual sensor units perform: data acquisition, data development, data storage, statistical analysis, and data transmission. A set of sensor units deployed in proximity to each other can be designated as a group and act as a distributed sensing network with consistent and reliable data flow to a router and further to a central computer for extended data synthesis, analysis, and decision support. The group deployment facilitates achieving enhanced security and wider sensing capability.

35 Claims, 16 Drawing Sheets

U.S. PATENT DOCUMENTS

Figure 1A:
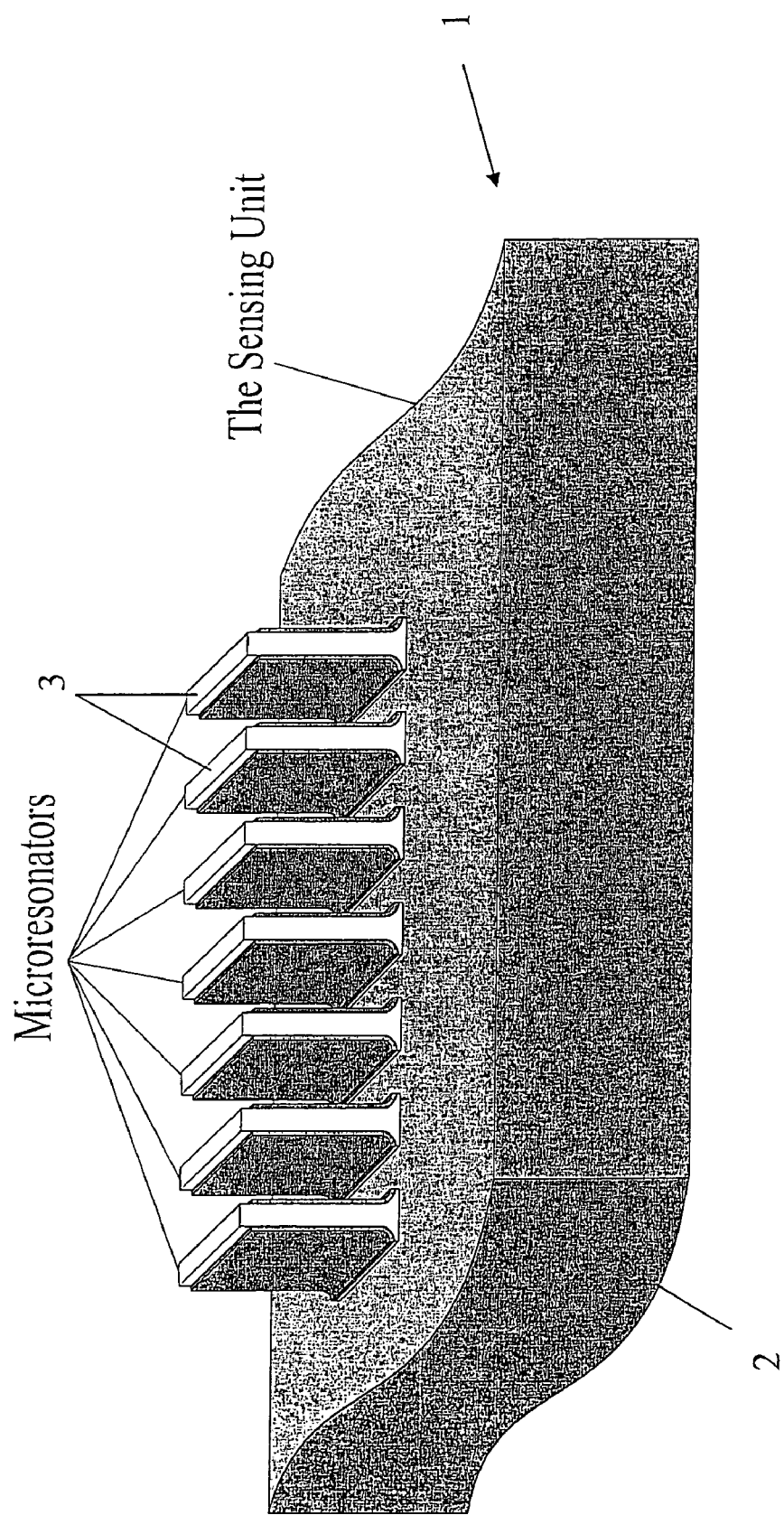
Figure 1B:
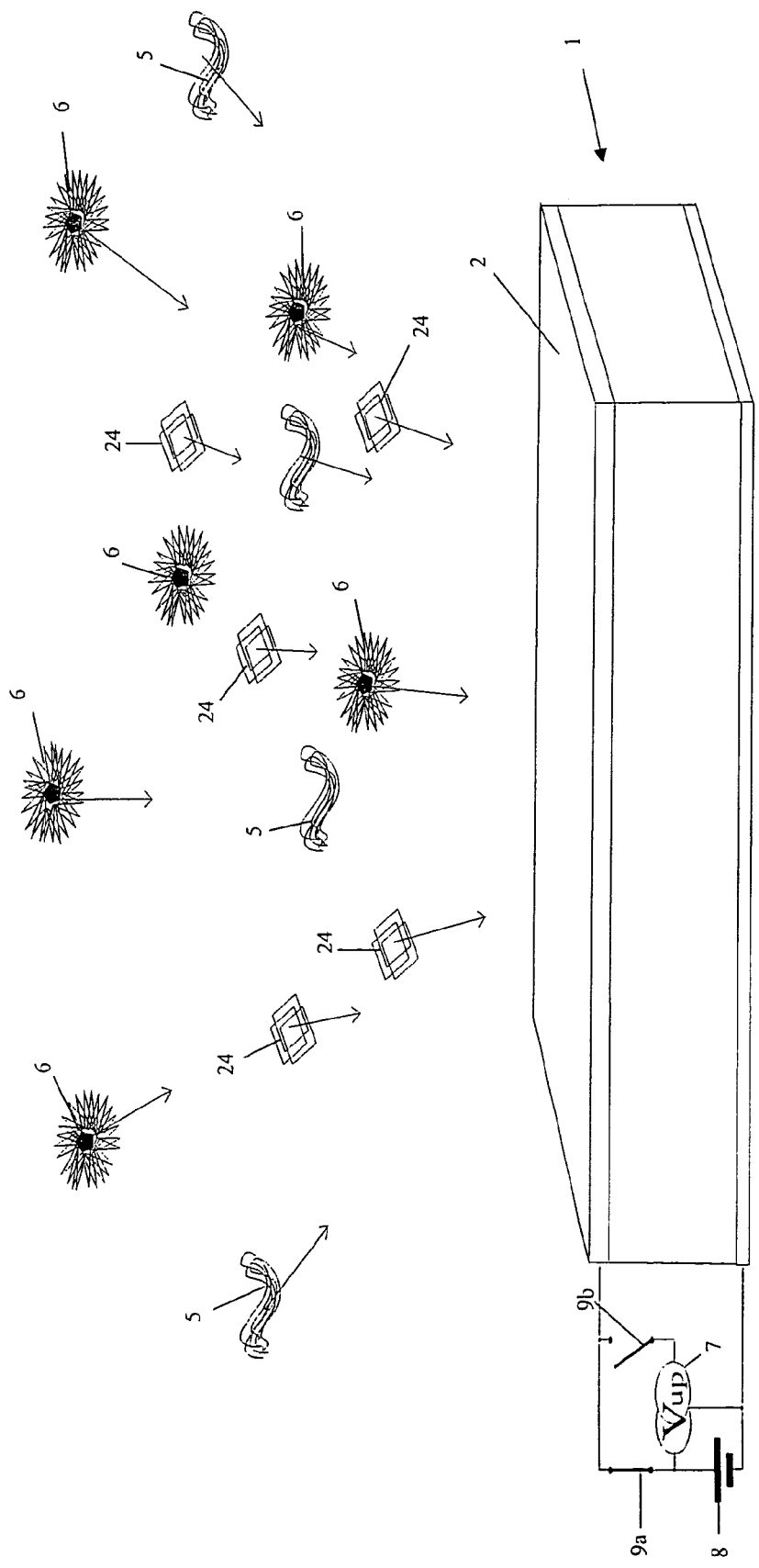

| | | |
|---|---|---|
| 6,699,667 B1 | 3/2004 | Keen |
| 6,701,772 B1 | 3/2004 | Kreichauf et al. |
| 6,703,819 B1 | 3/2004 | Gascoyne et al. |
| 6,706,479 B1 | 3/2004 | Saraf et al. |
| 6,716,394 B1 | 4/2004 | Jensen et al. |
| 6,730,212 B1 | 5/2004 | Yamagishi et al. |
| 6,824,974 B1 | 11/2004 | Pisharody et al. |
| 6,829,073 B1 | 12/2004 | Krol et al. |
| 6,838,292 B1 | 1/2005 | Rajan et al. |
| 6,848,295 B1 | 2/2005 | Auner et al. |
| 2002/0042070 A1 | 4/2002 | Saraf et al. |
| 2002/0068018 A1 | 6/2002 | Pepper et al. |
| 2002/0167003 A1 | 11/2002 | Campbell et al. |
| 2002/0172963 A1 | 11/2002 | Kelly et al. |
| 2002/0192680 A1 | 12/2002 | Chan et al. |
| 2003/0013185 A1 | 1/2003 | Saraf |
| 2003/0045019 A1 | 3/2003 | Kubena |
| 2003/0054355 A1 | 3/2003 | Warthoe |
| 2003/0073071 A1* | 4/2003 | Fritz et al. ................... 435/4 |
| 2003/0134433 A1 | 7/2003 | Gabriel et al. |
| 2003/0166039 A1 | 9/2003 | Hubler et al. |
| 2004/0015336 A1 | 1/2004 | Kulesz et al. |
| 2004/0016287 A1 | 1/2004 | Fu |
| 2004/0023236 A1 | 2/2004 | Potter et al. |
| 2004/0025336 A1 | 2/2004 | Kulesz et al. |
| 2004/0029183 A1 | 2/2004 | Liebholz et al. |
| 2004/0064260 A1 | 4/2004 | Padmanabhan et al. |
| 2004/0072208 A1 | 4/2004 | Warthoe et al. |
| 2004/0110128 A1 | 6/2004 | Hannah |
| 2004/0113144 A1 | 6/2004 | Brousseau, III |
| 2004/0119591 A1* | 6/2004 | Peeters ................... 340/539.26 |
| 2004/0164859 A1* | 8/2004 | La Spisa ............... 340/539.26 |
| 2004/0191765 A1 | 9/2004 | Mozdy et al. |
| 2004/0197932 A1 | 10/2004 | Hsieh et al. |
| 2004/0200734 A1 | 10/2004 | Co et al. |
| 2004/0204915 A1* | 10/2004 | Steinthal et al. ............ 702/188 |
| 2004/0235016 A1 | 11/2004 | Hamers et al. |
| 2005/0018944 A1 | 1/2005 | Mozdy |
| 2005/0069864 A1 | 3/2005 | Utoh et al. |

\* cited by examiner

Phase 1: Collecting.

Phase 2: Analyzing.

Phase 3: Clean-up.
Acoustic and/or electrostatic shock.

Synchronous particles Transfer.
One sensing unit in phase 3 (cleaning)
another sensing unit in phase 2 (collection).

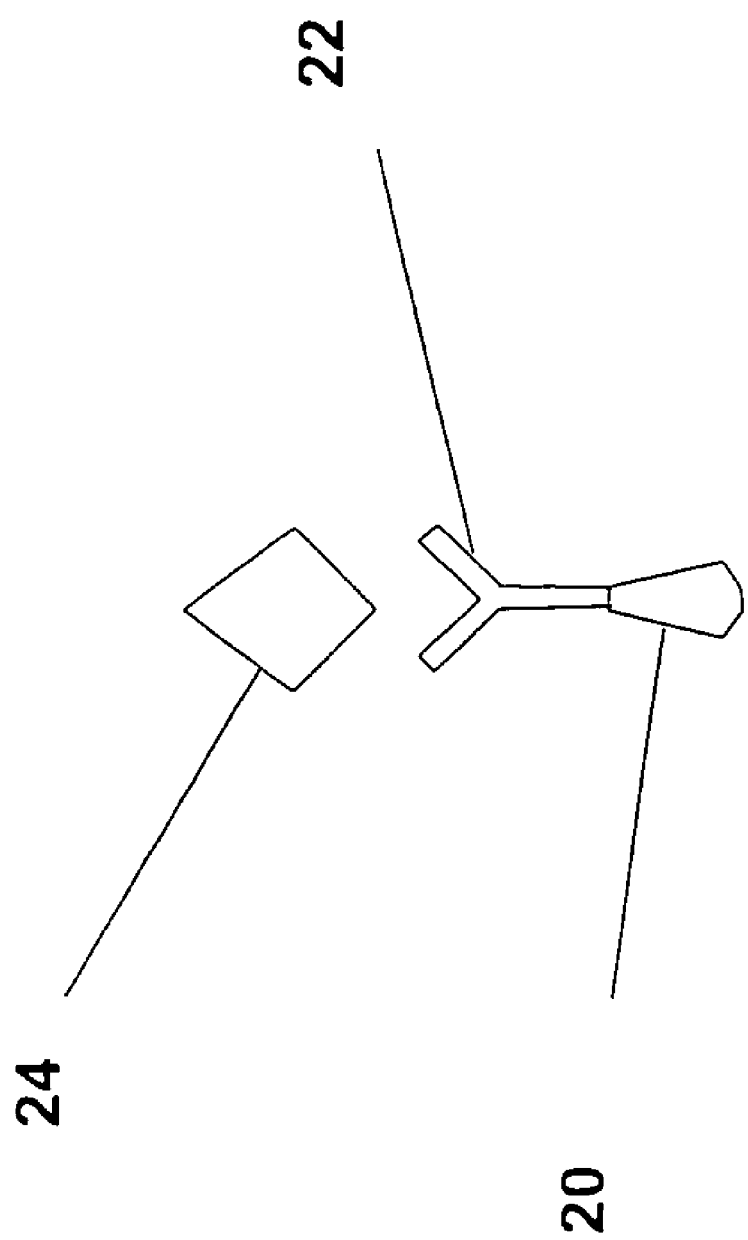

METHODOLOGY AND APPARATUS FOR THE DETECTION OF BIOLOGICAL SUBSTANCES

This application is a divisional of U.S. application Ser. No. 10/988,709, filed on Nov. 16, 2004, which claims priority to provisional application 60/523,303 filed Nov. 20, 2003.

FIELD OF THE INVENTION

The present invention is directed to a miniaturized sensor and group of sensors sensitive to various biological substances such as viruses, bacteria, spores, allergens and other toxins as well as a system for analyzing the outputs of the sensors.

BACKGROUND OF THE INVENTION

It is unfortunate that the public, in the last several years, has witnessed an increased level of terrorism both within the borders of the United States as well as in the rest of the world. Although the attacks of Sep. 11, 2001 were monumental in scale and destruction, the public has been made aware that various other types of attacks, such as on a more microscopic level could occur. The mailing of anthrax laden correspondence to various of our public officials have only heightened the concern that various biological substances may be employed in devastating fashion.

Therefore, it is of utmost importance that a system of sensors be developed to provide an early warning against the possibility of such biological warfare.

SUMMARY OF THE INVENTION

The problems associated with preventing the widespread use of biological warfare are addressed by the present invention which utilizes a self-contained, millimeter-scale sensing and communication platform for a massively distributed sensor network with flexible network hierarchy and secure data flow. Individual sensor units in the form of chips are designed and manufactured in the size of a grain of sand and contain sensors, a processor unit, a memory, bi-directional wireless communications, and an internal power supply. Each sensor unit is controlled by a self-contained microcontroller in the form of a digital signal processor (DSP). This DSP controls both tasks performed by the sensor chip and, to conserve energy, power management between and for the various components of the system. Periodically, the DSP receives a reading from the sensor unit provided with one or more sensors contained on the chip, processes the data received from the sensors, and stores results in its memory. It also pseudo randomly activates the optical, acoustical and/or radio frequency (RF) transceiver provided on each sensor unit to monitor for incoming communication attempts. This communication may include new programs, data or messages from/to other sensor units or from/to a base station router(s) which controls the operation of a plurality of sensor units. In response to a message or upon initiation of a message, the DSP will use the RF transceiver, room re-transmitter (field operation station), or laser to transmit sensor data or a message to the router, another sensor unit or a centralized station. The router would also direct communication to or from the centralized station. To address the detection of different kinds of biological substances such as viruses, bacteria, allergens, molds, proteins, and toxins (collectively, "targets"), the invention incorporates two classes of sensors with totally different manners of sensing and acquiring information.

The first of these sensors is acoustically based and may be used repeatedly without degradation. This sensor is functionally dependent on acoustical wave technologies. The sensor portion of the sensor unit is constructed as a microminiature mesh (net) on a silicon base, and has its own resonant frequency. For more accurate resonance readings other elements such as sapphire, quartz, or a germanium silica oxide (GSO) crystal, or a beryllium silica oxide (BSO) crystal may be used. The surface of the sensor unit is relatively small, approximately 1 mm$^2$ of working surface. To achieve greater sensor sensitivity and selectivity to the targets, both sides of the sensor unit base are charged by static electricity. The acoustically based sensor unit operates in three primary modes—collecting data, measuring data, and cleaning the sensor unit. During the collecting mode, targets come in proximity to the sensor. The static electricity applied to each sensor unit surface will draw the targets toward the surface of the sensor and will stick to the sensor unit surface due to molecular adhesion forces. After a time increment determined by a timer provided in the DSP, the sensor unit will be switched to the measurement mode. At this juncture, static electricity will be switched off and the sensor surface will begin to resonate with high frequency oscillation conditions. If there are no targets adhered to the sensor unit surface, the surface will resonate at a first frequency. The sensor surface will resonate at a second frequency, unequal to the first frequency in the presence of particular targets. The power and frequency of that oscillation will be a function of the physical properties of the target particles. The oscillation would result in the target particle leaving the surface of the sensor, resulting in the generation of a pulse. The acoustical nature of the pulse will be analyzed by the DSP and compared to data contained in a data base provided in the memory of the DSP. If any matching properties are found, this information will be relayed to the centralized station which could issue an alert. During the cleaning mode, the surface of the sensor will be cleaned by the simultaneous application of static electricity depolarization and high power pulses, at a third frequency. After cleaning, all modes may be repeated as required.

Sensor units will be calibrated to known target signatures. If the air has a preponderance of targets exhibiting the same or similar signature (mass, adhesion factor, form factor, etc.), an alert will be triggered providing the micro-biological identity of the particles. This alert would be produced based upon communication between sensor units themselves, between communication with the routers and the sensing units and communication between the sensor units, the routers and the centralized system.

Each sensor unit will be manufactured from silicon wafers on a sapphire, quartz, BSO, or GSO crystal base substrate, such as those currently used for manufacture of microchips. All frontal surfaces will be used to produce and store energy.

The second type of these sensors would be a biological based sensor falling into two categories; bio pore sensors and the optical based sensors. Bio pore sensors are microminiature pools made up of pores containing substances (ligands) preferably in gels or other substances, and electro-sensing technologies. These bio pores contain the ligand in gel resting on electrodes that will react based on the presence of one simple molecule of a target. During the reaction, the bio pore will produce an electric signature pulse and static electricity, which will be analyzed and trigger an alert if a particular target is present. This analyzation would include comparing the electric signature pulse with a plurality of electro signature pulses stored in the memory of the DSP. This technology will require biological data sets documenting the reactive ligand for each target. This data will be used to choose the gel substances for the bio pores. In all other ways, including data acquisition, data processing, and data communication, operational implementations are identical for any target.

Biological optical based sensors will have much in common with bio pore sensors. The main difference in their design is the integration of light-sensing micro-systems to detect and discriminate the sequence of photon bursts generated at the interaction of the target and ligand. These photon-bursts would be in the form of electro-optical signature pulses, compared to a plurality of electro-optical signature pulses stored in the memory of the DSP.

BRIEF DESCRIPTION OF THE DRAWINGS

The foregoing generalized description of the invention will be better understood from the following detailed description of preferred embodiments of the invention with reference to the drawings that include the following:

FIG. 1A is a diagram of an acoustical based sensing unit;

FIG. 1B is a diagram of the acoustical based sensing unit of FIG. 1A in the collecting mode;

FIG. 1C is a diagram of the acoustical based sensing unit of FIG. 1A in the analyzation mode;

FIG. 1D is a diagram of the acoustical based sensing unit of FIG. 1A in the cleaning mode;

FIG. 1E is a diagram of two acoustical based sensing units, each in a different mode of operation;

FIG. 2 is a diagram of a bio pore sensor;

FIG. 3 is a diagram of the bio pore sensing unit and a field effect transistor (FET) used to sense a reaction between a ligand and a specific target;

FIG. 4 shows the FET of FIG. 3 with the ligands encased in a gel;

FIG. 5 shows an alternate embodiment of the bio pore sensing unit and the FET shown in FIGS. 3 and 4;

FIG. 6 illustrates a bio pore sensing unit and an FET provided with two electrodes;

FIG. 7 illustrates an alternative embodiment of the bio pore sensing unit and FET with multiple nanotubes;

FIG. 8 represents a top view of a bio pore sensor;

FIG. 9 is a side view of the bio pore sensor shown in FIG. 8;

FIG. 10 illustrates a biologically optical based sensing unit;

FIG. 11 illustrates a typical DSP, according to the present invention; and

FIG. 12 illustrates the system according to the present invention.

DETAILED DESCRIPTION OF THE INVENTION

Each of the chips used as a sensor unit will be manufactured from silicon wafers on a sapphire, quartz, or BSO or GSO crystal base substrate or similar material, such as those currently used for manufacture of microchips. All frontal surfaces of the sensor units (except the bio pores) will be used to produce and store energy. The operationally integrated sensor units will act as a massively distributed sensor network. This network will function as a monolithic unit, providing a de-facto three dimensional real time sensing of the presence of biological substances. For instance, some clusters of sensor units could form a synchronous group executing on the same working cycles, thereby increasing the sensitivity and reliability of the system, and creating special features such as a distributed antenna. The invention lends itself to customization, and is readily adaptable to diverse operational configurations. For example, clusters of units could be aligned to monitor a statically charged air pump which will move air, which could include targets, in one specific direction. This will increase the sensor sensitivity because the target particles will be brought into closer proximity with the sensor units. This system exhibits reliable capabilities to sort all targets using static electricity. This invention capitalizes on the fact that all target particles saturated in the air do not react equally to the polarity of the static electricity charge. Groups of the sensor units will change polarity together, generating additional information about the target distribution in air, such as how the air in a ventilation system is moving. This will create the basis for relational databases mapping the nature of the target to atmospheric conditions.

Referring to the drawings, FIG. 1A illustrates an acoustical based sensor 1 having a sensor unit 2 comprising a plurality of micro resonators 3 on the surface of the sensor unit, thereby forming an oscillating web. FIGS. 1B, 1C and 1D illustrate the operation of the acoustical based sensor 1 in the collecting mode shown in FIG. 1B, the analyzation mode illustrated in FIG. 1C and the cleaning mode detailed in FIG. 1D. The acoustical based sensors as well as all of the other sensors described in the present invention are adapted to be applied to the surface of a product, such as medical equipment, clothing or food or are adapted to be air borne. Regardless of whether the acoustical based sensors or biological based sensors are affixed to an object or are drifting in air, the purpose is to detect the presence of one or more of a plurality of biological substances denoted as "targets" 24 which would be harmful to humans and/or animals. These targets 24 would generally be air borne along with various other floating matter such as protein strings 5 and dust particles 6. The acoustical based sensor 1 would be characterized as a sensor unit 2 having a surface onto which the various particles 5, 6 and 24 would settle. The surface unit would be connected to a DC current source 7 having a battery 8. Two switches 9*a*, 9*b* would be attached in parallel to the source of electricity. Therefore, in the collecting mode as shown in FIG. 1B, electricity would be applied to the surface of the sensor unit 2, allowing the sensor unit to oscillate at a first frequency. The switches would be in the position shown in FIG. 1B to apply a first current level to the surface of the sensor unit to allow that sensor unit to oscillate at that first frequency and power. As shown by the arrows attached to each of the air borne elements 5, 6 and 24 shown in FIG. 1B, these air borne elements would become attracted to the surface of the sensor unit.

Once these particles 5, 6 and 24 become attached, or rest upon the surface 2 of the sensor unit, switch 9*a* moves to the position shown in the analyzation mode shown in FIG. 1C, thereby removing the source of electricity from the surface of the sensor unit. At this time, the air borne particles which would include target particles 24 would begin to oscillate at a second frequency, different than the frequency in which the surface of the sensor unit would oscillate in FIG. 1B. A DSP including a bidirectional wireless communication, an internal power supply as well as a memory would sense the particular resonating frequency. This frequency would be compared to frequencies stored in the memory of the DSP, indicative of particular targets. If a match is made between the oscillating frequency of the target or targets and the oscillating frequency stored in the memory of the DSP, this match would be noted and stored in the memory of the DSP. At that time, or at a later time, this information would be transmitted utilizing the particular communications capacity of the sensors to adjoining sensors, to one or more routers, or to a centralized station in which a decision regarding the presence of toxic biological substances, indicative of a bio terrorist attack would then create the appropriate alert.

Figure 1C:
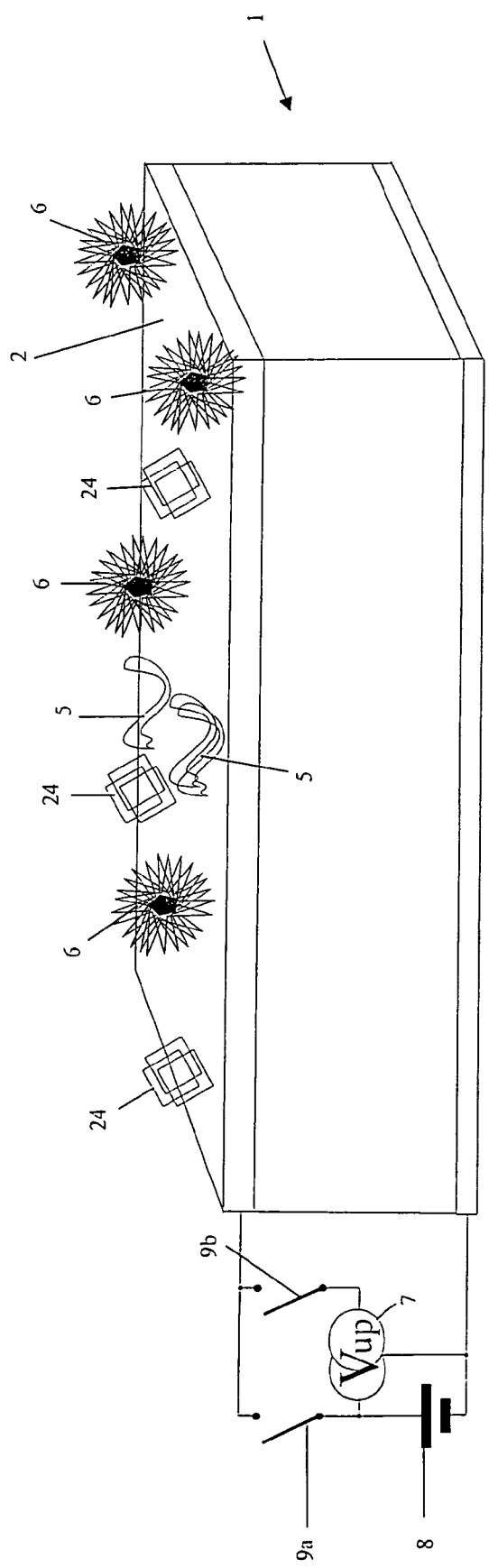
Figure 1D:
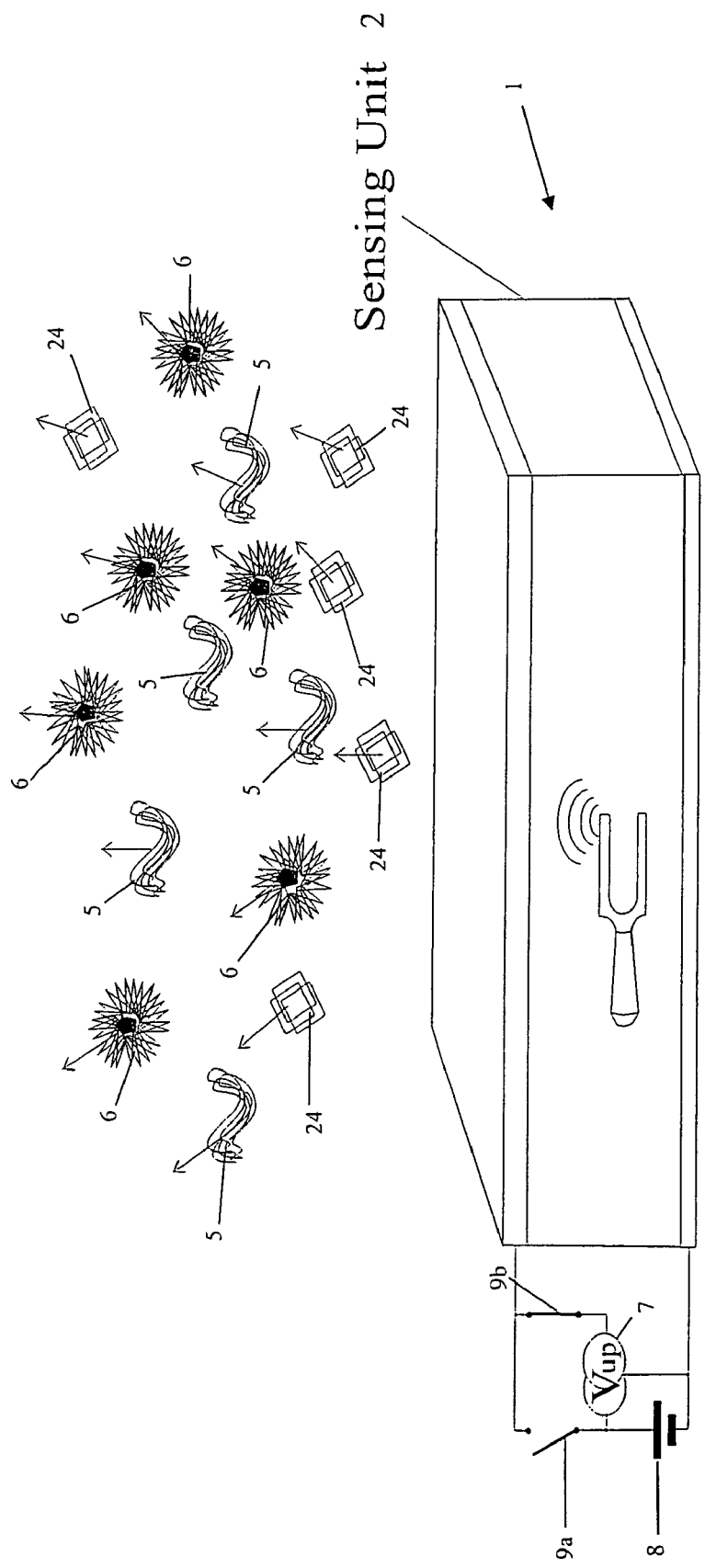

Once the analyzation step is complete as illustrated in FIG. 1C, the surface of the sensor unit 2 would be cleaned by moving switch 9b to the position shown in FIG. 1D. At this point, the surface of the sensor unit would oscillate at a third frequency, thereby ejecting all of the air borne material 5, 6 and 24 from the surface of the sensor unit as shown by the arrows included in FIG. 1D.

Figure 1E:
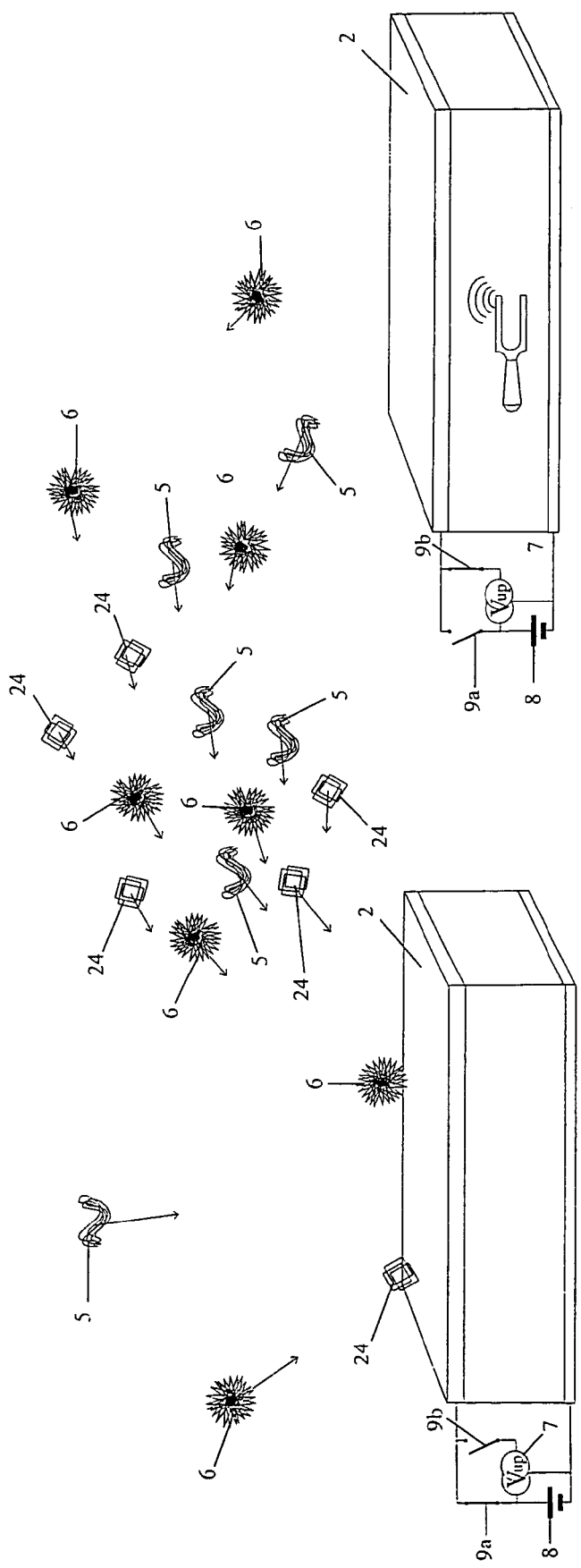

FIG. 1E shows two adjacent sensor units in differing phases such as the cleaning phase or the collection phase. The collection phase is illustrated by the sensor unit on the left and the cleaning phase is illustrated by the sensor unit on the right. The inclusion of the cleaning phase shown in FIG. 1D would result in enabling repeated use of the acoustical base sensor unit.

FIG. 2 shows a typical biological based sensor unit including a ligand 22 and a biological target substance 24. Additionally, an optional biological amplification unit 20 can be affixed to a non-sensing surface of the ligand 22. The ligand 22 is an ion or molecule that reacts to form a complex with another molecule. The target 24 is the molecule bound specifically by the ligand. Each ligand operates in conjunction with a specific target, of which there are a multitude of possible ligand/target pairs. The target may be a single molecule such as a protein, glycoprotein, saccharide, or lipid. The target may also be an organism such as bacteria or its spore, a virus, fungus, mold, or yeast. The ligand 22 and target 24 bind together with high affinity and specificity. Examples of ligand/target pairs are an antibody and whatever macromolecule the antibody was generated against, a cellular receptor and whatever substance specifically binds and activates the receptor, or a surface feature on a microorganism such as hemaglutinin on an influenza virus and an antibody or molecule (such as sialic acid in the influenza example) that binds the surface feature. It is important to note that a target will only completely attach itself to only one type of ligand. An interaction by the ligand with a target to which it should not bind completely, would result in, at best, only a partial binding, for an instant of time.

Interactions between a ligand and its target arise from intermolecular attractions that include complementary conformations, charges, polarities, Van der Waals interactions, and reordering of the water molecules in the surrounding millieu. These attractive forces are cooperative and accumulate as the target and ligand come in proximity. Each target/ligand interaction has a specific kinetic and thermodynamic signature that can be characterized and quantified:

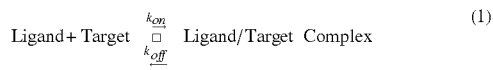

(1)

The equilibrium constant is derived from the relation of the on and off constants:

$$K_{eq} = k_{on}/k_{off} \quad (2)$$

$K_{eq}$ is related to free energy by $\Delta G = \Delta G° + RT \ln K_{eq}$, and at equilibrium $\Delta G = 0$, so:

$$\Delta G = -RT \ln K_{eq} \quad (3)$$

For $K_{eq} = 1$, $\Delta G° = 0$

For $K_{eq} = 10$, $\Delta G° = -1.4$ Kcal/mole

For $K_{eq} = 10^5$, $\Delta G° = -7$ Kcal/mole with
R=universal gas constant
T=temperature (Kelvin Scale)

The $K_{eq}$ for avidin-biotin interaction is approximately $10^{15} M^{-1}$, and for a "typical" antigen-antibody interaction is approximately $10^{12} M^{-1}$. Thus the energy released from a mole of avidin-biotin interaction is approximately 21 Kcal/mole and for antigen-antibody approximately 16 Kcal/mole. The unique pattern of energy release is a function of the interaction signature for each ligand/target pair.

The bio pore sensor unit shown in FIG. 2 is based on micro-miniature pores of ligands generally, but not necessarily embedded within aqueous gels on sensor unit surfaces with electro-sensing technologies cumulatively called bio pores. Each bio pore is filled with one or more ligands in gel and will react to the presence of one single molecule of a specific target for that ligand. During reaction, the reaction between the ligand and the specific target molecule will produce an electric pulse signature and static electricity which will be analyzed and trigger an alert if the proper target is present. This technology will require biological data sets describing the electrostatic signature generated by binding of each ligand/target pair. This data will be used to differentiate among targets. In all other ways, including data acquisition, data processing, and data communication, all implementations are identical to other ligand/target pairs.

The materials and methods disclosed herein provide an effective manner for the mass production of uniform micro fabricated units. To customize a deployment of units to a particular target(s) of interest (Hepatitis C, Salmonella, Anthrax, etc.), the bio pores will contain the appropriate and unique reactive ligand(s). More specifically, each sensor unit of the present invention comprises a signal-converting element, a transducer, a responsive element, and the ligand (shown in FIG. 2). Conversion circuits will include electron sensitive circuits, photosensitive based circuits, acoustic sensitive based circuits, and inductivity sensitive detection circuits, based upon the type of sensor utilized. Depending on the application, specific bio-amplification elements may be used. The signal-converting element is comprised of an active moiety and signal-transforming domain. The ligand-specific moiety specifically recognizes a selected target. A sensing unit used with the ligand shown in FIG. 2 would include software and hardware to monitor and detect specific targets. Depending on the preliminary detector conversion circuits, the bio-amplification or device 20 may or may not be used. For instance, in some cases, when dealing with an extremely low energy ligand/target interaction, a sensing element with amplifier 20 such as enzymatic fluorescence or chemiluminescence generation, with a photon-sensitive detector can be employed. In this case, after detection by the sensing unit, an electrical pulse will be converted to a photon stream, which will be detected by a sensitive photo-detector.

Figure 3:
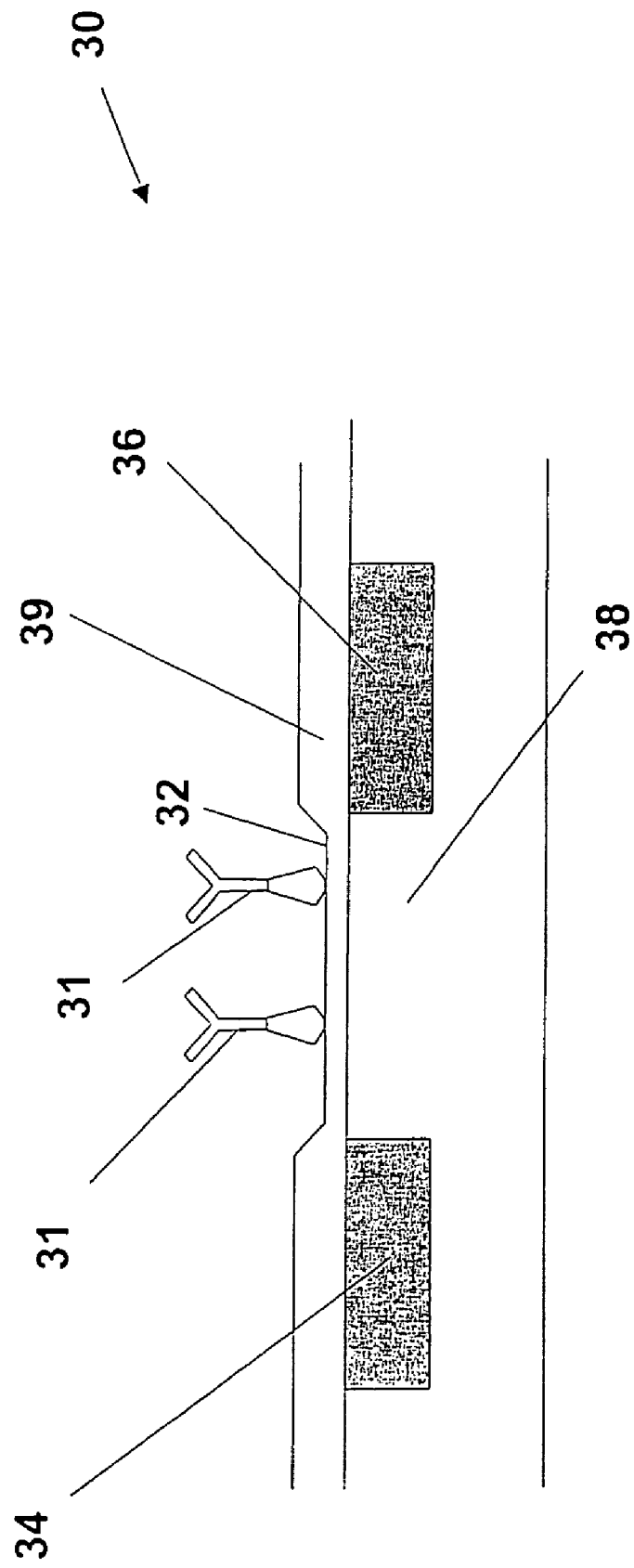

FIG. 3 represents the use of a field effect transistor (FET) 30 with a sensing gate 32 as a measurement device awaiting integration of the gel and molecules of a ligand 31. The ligand 31 is placed on or close to the gate 32 as possible, such that any ligand/target interaction will generate a current from the source area 34 through the gate 32 to a drain area 36. The FET is provided on a semiconductor base 38. A layer of insulation 39 is provided over the gate 32, the source 34 and the drain 36. This FET structure will be implemented in several formats as will be discussed. The FET structure can take the form of a miniature electron sensitive field effect transistor (ESFET).

Figure 4:
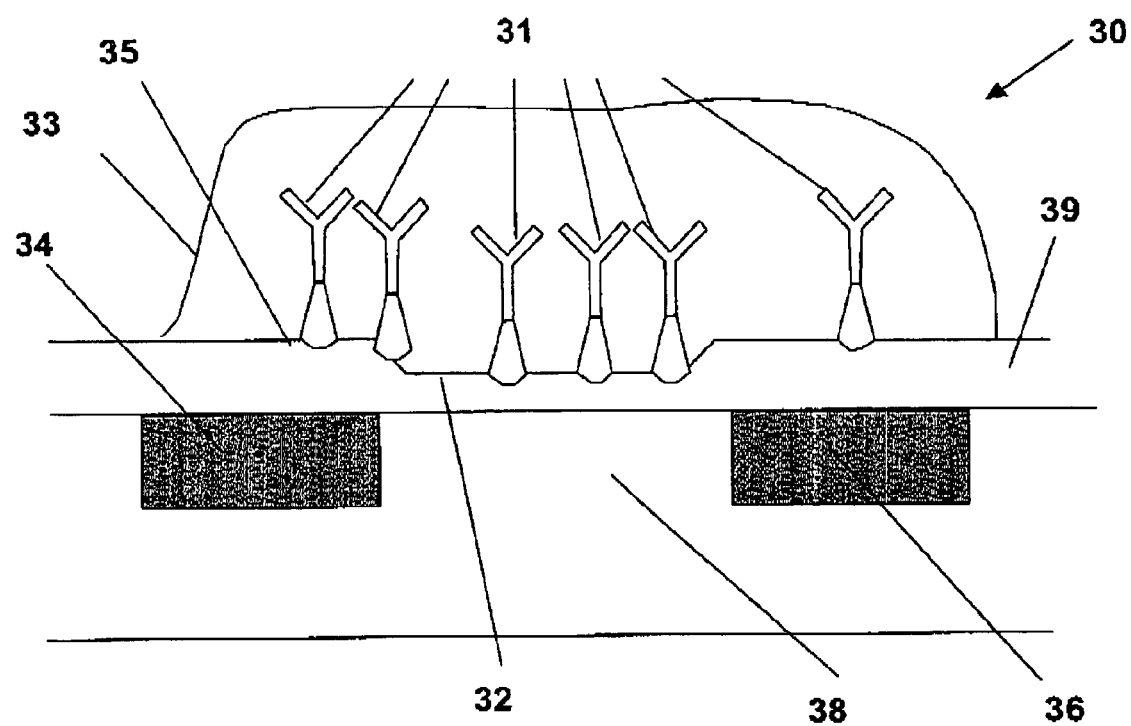

FIG. 4 depicts the FET 30 with gel 33 incorporated in the design. The gel utilized should exhibit the properties of remaining moist, having optical sensitivity and allowing the targets to pass through the gel and to bind to the ligand. There are several ways to place the ligand in operational proximity to the gate area. For instance, the surface of the gate 32 can be coated with aminosilane. The ligand is tethered to the amino groups via a variety of cross linkers 35, for example, disuccinimidyl suberate, Bhydroxy disuccinimidyl suberate, etc. The cross linkers can be chosen with specificity to selected functional groups on the ligand to achieve the desired orientation.

Figure 5:
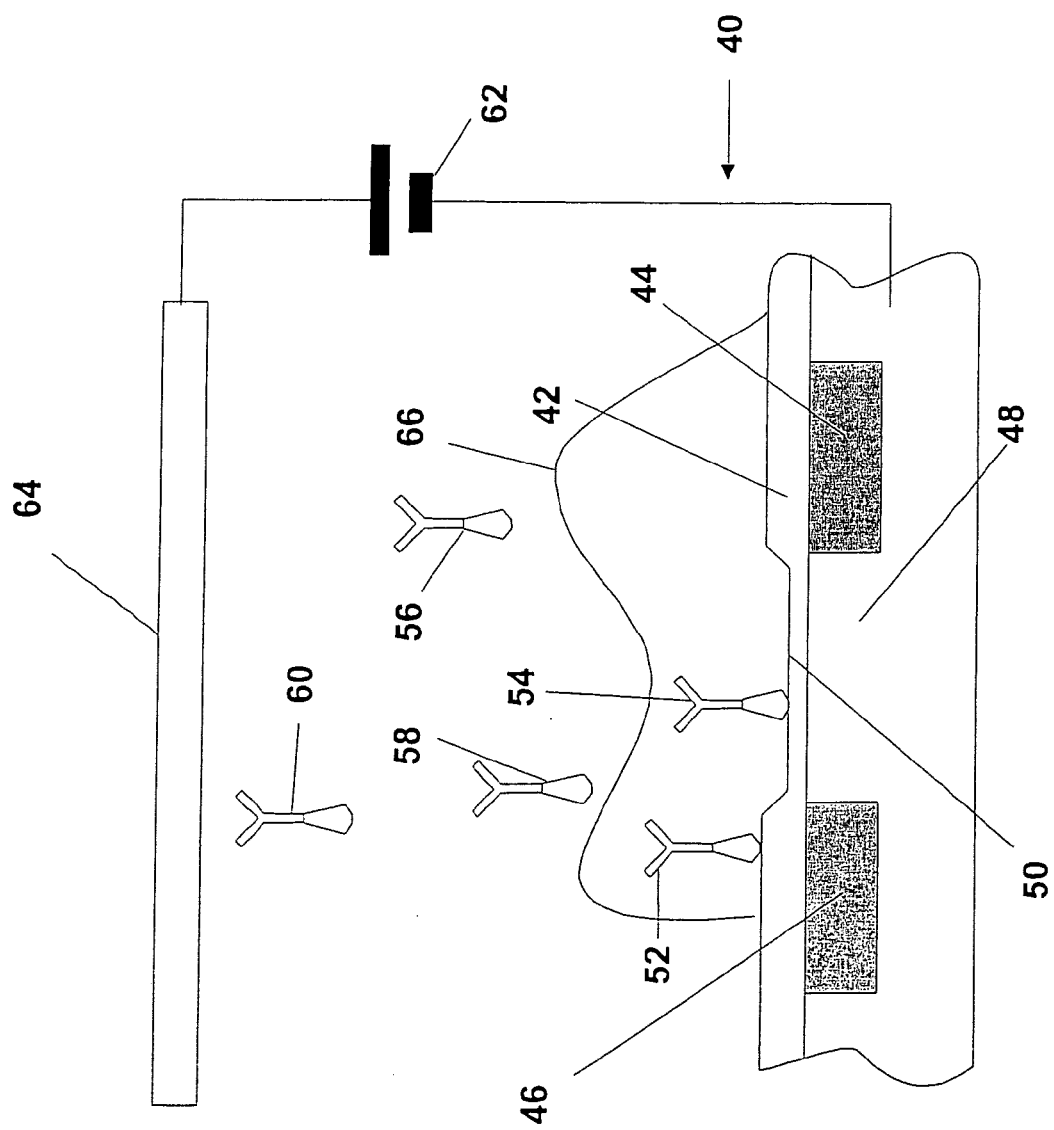

FIG. 5 depicts an alternative embodiment of the FET approach. This FET 40 includes a silicon base 48 on which a source area 46 and a drain area 44 are provided. A gate 50 is provided on an insulator 42. A number of ligands 52, 54, 56, 58 and 60 are associated with the FET 40. These ligands are captured with a DC field produced by a DC current source 62 and an electrode 64. AS was true with the FET shown in FIG. 4, a similar gel 66 will be incorporated in the design. This facilitates orientation of the sensing elements to provide optimal sensing capability.

Figure 6:
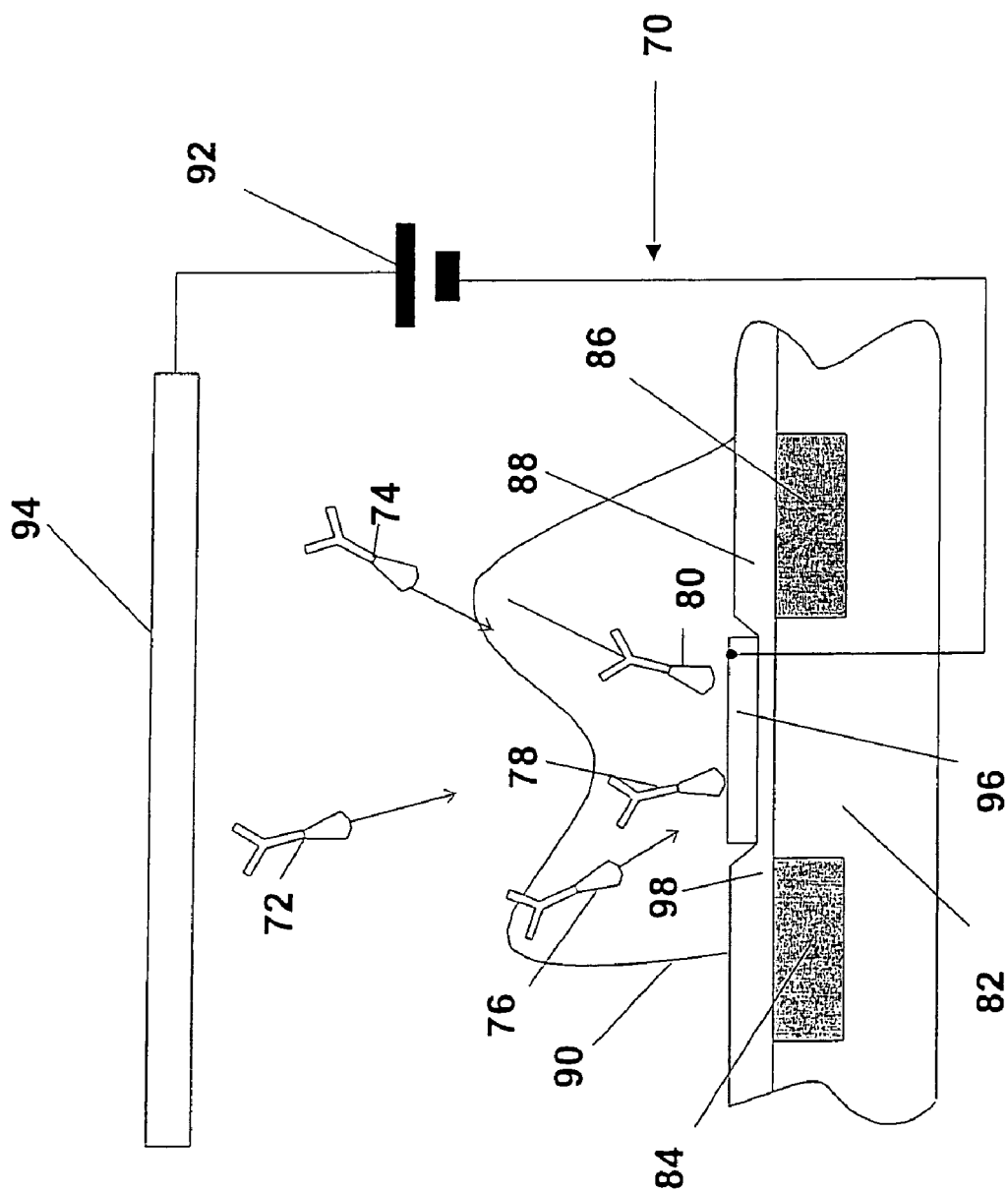

FIG. 6 depicts an alternative approach FET 70 to facilitate orienting the ligands 72, 74, 76, 78 and 80, electrostatically prior to introduction of the gel 90. Besides orienting the ligands, the dual electrode configuration including a DC current source 92, an upper electrode 94 and a lower electrode 96 in proximity to the gate area 98 will facilitate movement of the ligands to the gate area 98, ultimately attaching them to the lower electrode 96 in the area of the gate area. The sensor unit includes a silicon base 82, a source area 84 and a drain area 86 and a layer of insulation 88. The lower electrode 96 will then completely dissolve, permitting the FET to function normally. Alternatively, the lower electrode will be only partially dissolved, facilitating a bias feedback capability.

Figure 7:
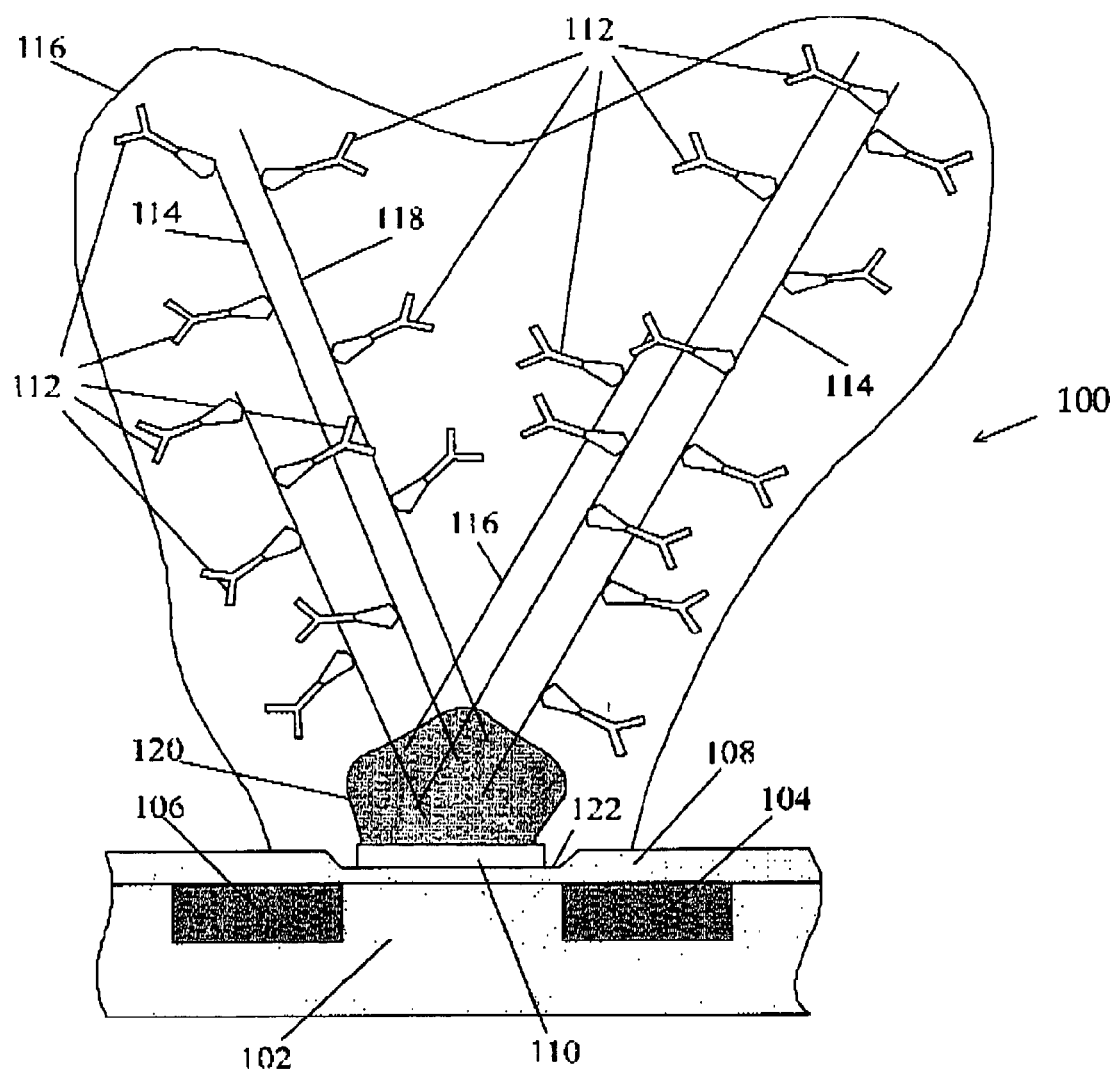

FIG. 7 depicts an advanced FET sensor 100 incorporating one or more catalyst islands 120 positioned on the FET gate electrode 110 in the area at the gate 122. The catalyst island is capable of growing nanotubes 114, 116, 118. The FET 100 includes a silicon base 102, a drain area 104, a source area 106 and an insulation coating 108. The catalyst island 120 consists of chemical ingredients that form a base for growing the nanotubes. Nanotubes typically grow in a chaotic manner. Their ultimate quantity and volume are managed by controlling time and temperature. The responsiveness to time and temperature are dependent on the ingredients of the catalyst. Generally, multiple nanotubes will be grown. The surface of the nanotubes can be customized using alternative methods to modify their properties. Modification can be achieved using chemical solutions to etch the nanotubes surfaces. Alternatively, the nanotubes can be coated with chemicals. The primary configuration for this invention will include coating the nanotubes with conductive or semiconductive materials. This will be followed by application of the gel. This dramatically increases the surface area for target detection without increasing the linear surface of the detector. Operationally, after the ligand/target interaction, the signal will come through the surface of the nanotubes to the gate of the FET. Since the nanotubes are indirectly in contact with the gate of the FET, and the ligands would adhere to the surface of the walls of the nanotubes, more ligands would indirectly be in contact with the measurement device, i.e. the gate area. Operation then proceeds as previously described.

Figure 8:
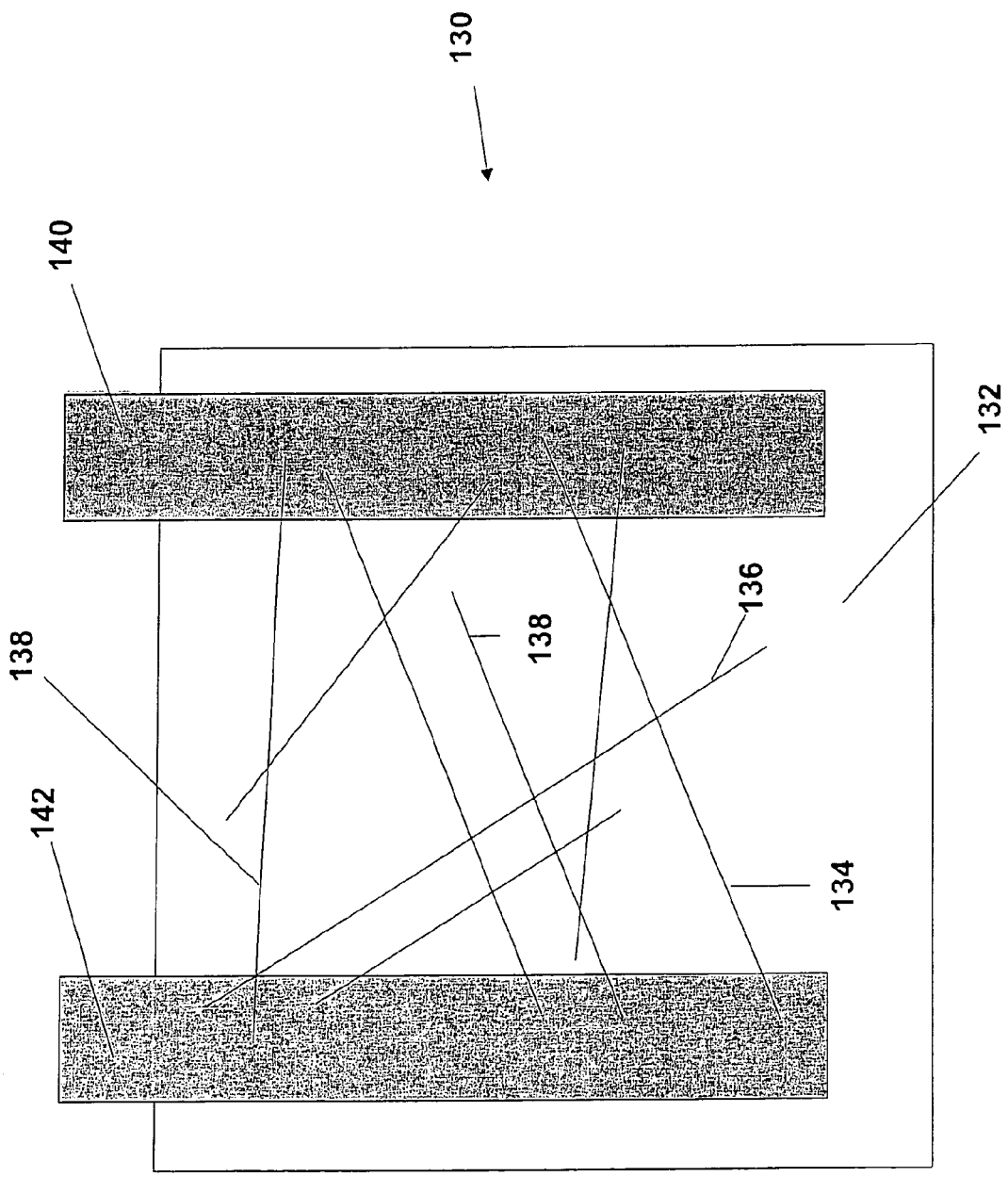

FIG. 8 presents one possible implementation of the bio pore sensor 130. In this case, the pore 132 has been created on the silicon chip surface. In the bio pore, nanotubes 134, 136, 138 generally extend between two electrodes 140 and 142. All surfaces of the nanotubes will be covered with metal (clayed or plaque). The result is a dense electrode mesh. The pore is filled with many ligand elements connected to the nanotubes. When contact between a ligand and a target is achieved, a signal will be propagated over the nanotube mesh and to the electrodes 140, 142. Electrodes are connected to the registration circuits (not shown).

Figure 9:
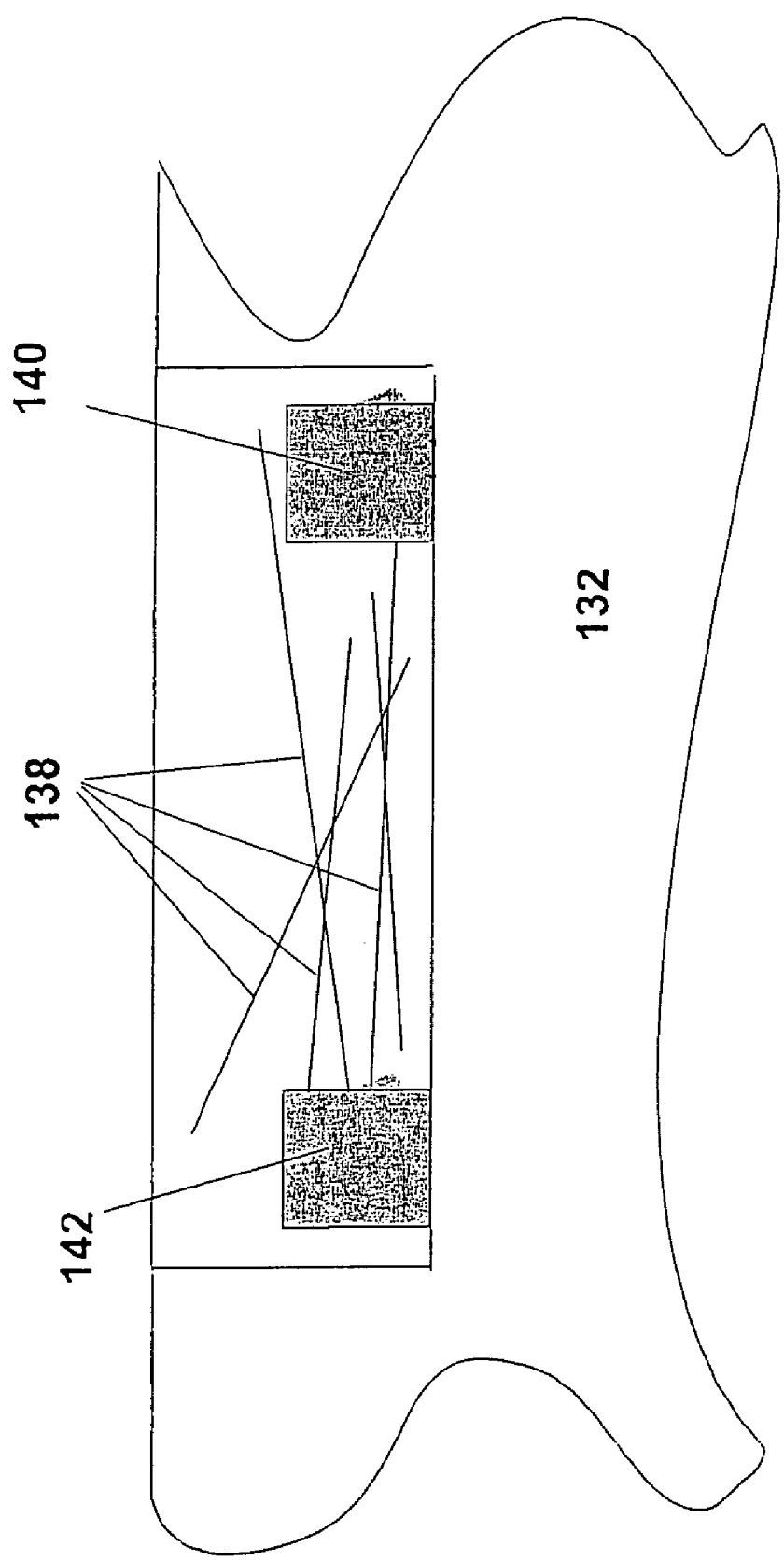

FIG. 9 depicts a side view of the bio pore 132 and a multidimensional perspective of the relative locations of the electrodes 140, 142 and the nanotubes within the pore. There are multiple configurations for the various components that constitute a bio pore. The optimal configuration is a function of the planned deployment. These configurations will not be limited by availability of materials. It has been shown that available materials retain their film-forming properties even when non-latex water-soluble components (e.g., proteins, enzymes, polysaccharides such as agarose, or synthetic polymers) comprise up to approximately 25% by weight of the material. This alleviates a significant consideration related to a micro fabrication process for the production of biosensors; the established film adheres effectively to a planar substrate even in the presence of large amounts of additives (i.e., enzymes). Particle latex materials have been used traditionally to immobilize all manner of biologically active materials. Thus, the biosensor units of the present invention provide a flexible, generic system that can be adapted to recognize any selected biological substances.

Figure 10:
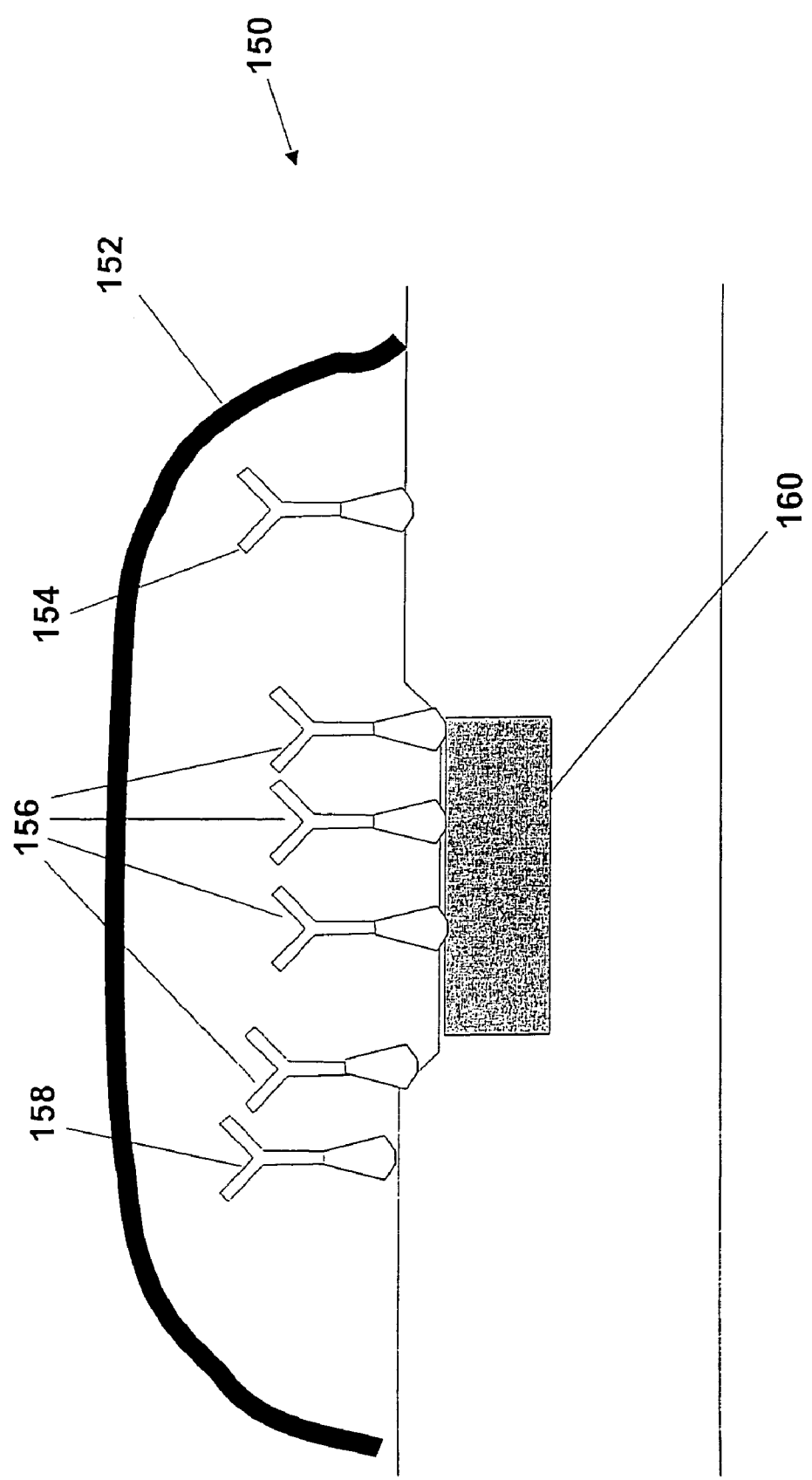

A biological optical based sensor is shown in FIG. 10. It is based on micro-miniature bio pores made up of pores of gel 152 containing ligands 154, 156, 158 and a light-sensing detector 160. During the interaction of the target with the ligand, a sequence of photon bursts or signatures will be generated and detected by the light-sensing micro-system including detector 160. The micro-systems will be built based on Avalanche Diodes type, Charge Coupled Devices (CCD), or other light-sensing technologies. Upon detection, a comparative analysis of the newly observed data and data stored in the DSP memory will be performed in the manner previously described with respect to the acoustical based and the non-optical based biological sensors.

Optical techniques have been successfully used in the field of sensors, monitoring reactions by measuring changes in absorption, fluorescence, scatter, and refractive index. In particular, for the biological optical based sensor, a layer which undergoes an optical change is integrated onto the surface of the device so that the evanescent field of the light penetrates the sensing layer. Monoclonal antibodies may be used as the sensing layer, with high specificity to defined targets, then changing the sensing layer composition. Any reactions occurring at the sensing layer affect the evanescent field and hence the optical properties of the device.

This biological optical based sensor will take advantage of interaction energy conversion to fluorescence, detecting the emitted light after interaction. The gel and the ligands in this detector will be located based on descriptions accompanying FIGS. 5 and 6.

Figure 11:
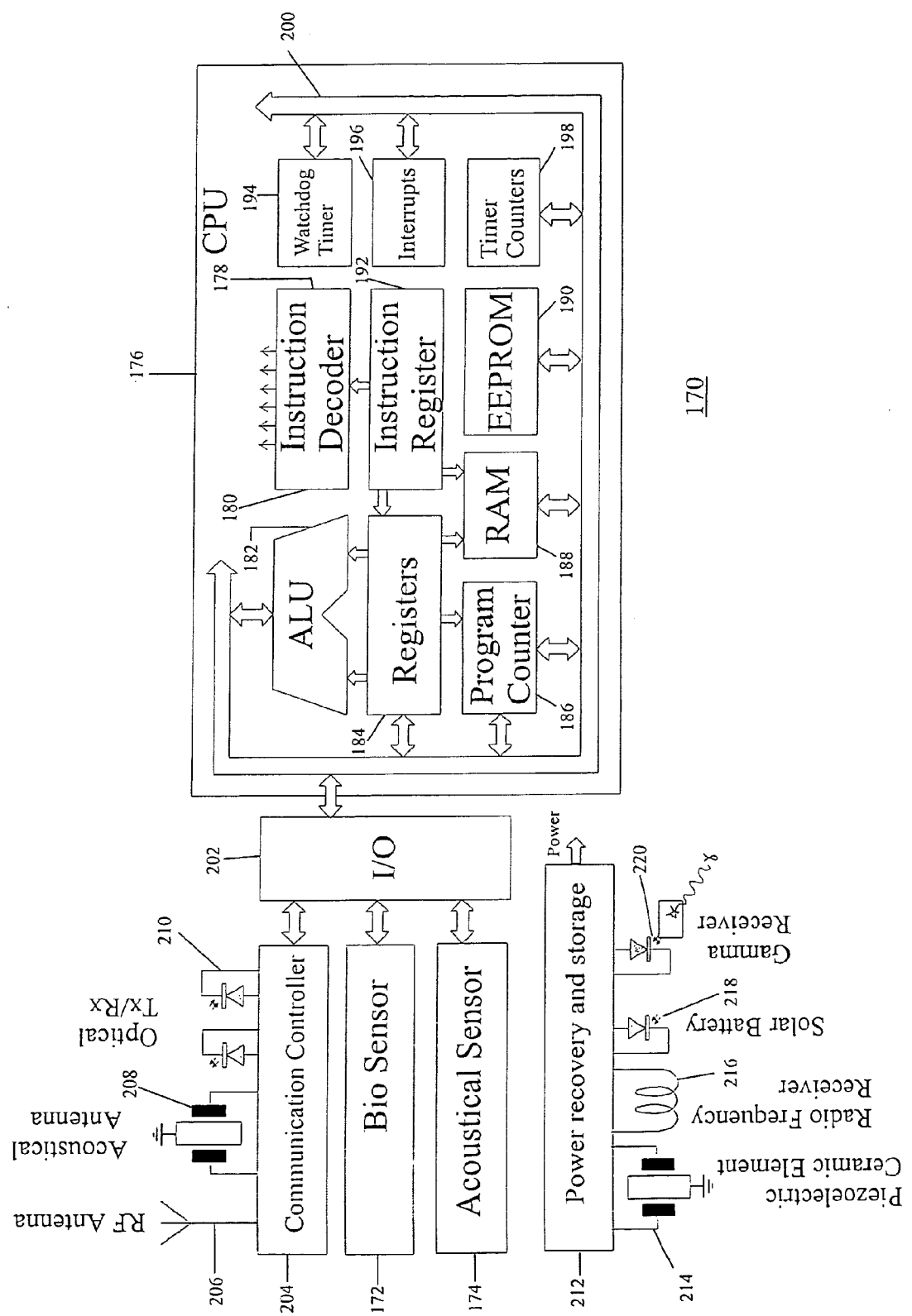

As previously described, each of the various types of sensor units would be provided with a DSP 170 as shown in FIG. 11.

Each sensor unit has a dedicated input/output channel 202 for initial power-up, charging the main storage capacitor, programming, and performance of test procedures. Connection to this channel will be done over dedicated devices, during initial test procedures. The input/output channel allows communication from each of the sensor units, such as the bio pore or bio optical sensor 172 and the acoustical sensor to a CPU 176, through a communication controller 204. Each unit has three additional channels: a near range (NR) communication channel including an acoustical antenna 208, a radio frequency (RF) channel including an RF antenna 206; and an optical channel including an optical antenna 210. The NR communication channel has an ultrasonic transmitter/receiver. This communication channel allows each sensor unit to communicate with nearby sensor units. In other words, the sensor units start to sense each other, exchange data packets, and even convey information data packets, as well as to coordinate the various operational modes employed by the acoustical based sensor unit.

The RF channel is intended to be used for middle range communication and cluster definition. This channel is faster and can convey more information in a given period of time. In some circumstances this channel could be used to communicate between sensor units, thus it is anticipated incorporating an RF processor to manage the data flow between sensor units.

The optical channel is mainly intended to partially, or in some circumstances, totally substitute for the main RF channel during long-range communication with the router or with large cluster-to-cluster communications as well as to the centralized station. If RF spectrum pollution is experienced, this channel, along with the NR channel, becomes the communication media.

Based upon the distances between the sensor units, the router and the centralized station including a computer, each of the aforementioned manner of connections can be used to disseminate information between the sensor units, the router and the centralized station computer.

A non-alterable memory read only memory (ROM) or an EEPROM 190 is provided in the DSP and consists of Programmed Logical Matrix (PLM) and controlling circuits. The primary intended use for the memory is to hold all operational programs and instructions. Additionally, the memory will hold some sample signature patterns of a number of targets. These signature patterns can be tailored to the type of sensor unit employed, or could include all of the possible signature patterns, regardless of the sensor unit.

A random access memory (RAM) 188 is also included in the DSP. The RAM 188 is used to hold variables, acquired data, temporary data, temporary variables, and other miscellaneous data.

A flash memory (not illustrated) is provided in the DSP. It is divided into functional groups including: a stack and stack pointer, variables and current states, additional program files, and data files. This memory is mainly used by an arithmetic logic unit (ALU) 182 for internal operations of the DSP. The ALU 182 can be used along with the EEPROM 190 and the RAM 188 to compare a measured signature with the signatures contained in the EEPROM 190.

The sensor units have some potential sources of interruption provided in the DSP. These sources of interruption include a watchdog timer 194, a wake-on-change 196; a real-time clock, various counters such as time counters 198 and a program counter 186, and overflow interrupts 196.

Each of the above-mentioned events generates a special signal to interrupt program flow and switch to the respective special attention functions. The watchdog timer 194 is the first tier of defense if an irresolvable DSP situation or any other event causes an unpredicted condition. This would be expected to occur most frequently if the processor is overwhelmed with different tasks and the power source capacity would not allow it to perform all functions simultaneously. Conceivably, the DSP could become trapped in an infinite loop with no normal manner to extricate itself. In this case the watchdog timer 194 will generate a high level interrupt to stop the loop and restart the DSP. Sensors and I/O channels produce a wake-on-change interrupt even during the power-saving sleep mode to allow the DSP to wake-up from an energy saving mode and assume the full operational mode. Overflow interrupts occur if corresponding flags in a special function register are enabled. The real-time clock is the main source of time synchronization. This interrupt allows performance of sequential operations with the DSP, its peripheral.

The sensor unit contains a 4-bit or 8-bit general-purpose ALU 182 performing arithmetic and Boolean functions between data in a working registers 184 and any register file such as instruction register 192.

The register files are divided into two functional groups consisting of special function registers and general-purpose registers. The special function registers are used by the DSP and peripheral components to control the operation of the device. The special function registers include the working register, a timer register, the program counter 186 and I/O registers. In addition, special function registers are used to control the I/O port configuration. The general-purpose registers are used for data and control information under command of the instructions.

The functions of the macro access controller (MAC) will be performed by the DSP. This will save power and space on the crystal, to optimize timing and avoid communication delays.

A bus 200 is included in the CPU 176 to allow for transfer of data to and from the components therein as well as to communicate with the I/O channel 202.

An RF processor in communication with the DSP provides synchronous and asynchronous communication modes for each sensor unit. The RF processor receives an RF synchronization sequence, determines the required action, adjusts receiving and transmission parameters, and receives and transmits data. The RF processor also optimizes power acquisition procedures.

Primarily for purposes of energy conservation, all RF related circuits are designed based on resonance based ideology, and are incorporated in close proximity on the chip. The current design includes compatible or semi-compatible spectrum and frequency requirements, as per IEEE 802.1xx standard, which will allow use of existing communication capabilities. There will be additional advantages for power acquisition in the given frequency range.

All amplification of signals are done at the minimum levels necessary to receive and transmit signals. Since there are strict power limitations, we assume all data transmissions include some data-loss. All data correction will be done within the DSP and its software. Thus, power conservation is the cornerstone of all operation and design.

The antenna field on each unit is symmetrical and occupies all available space on the chip's surface. Likewise, the antenna assumes the shielding function for all internal sub units. The size of the antenna and its geometry are functions of the frequency spectrum, proposed sensitivity, and transmission power level. The transmission power level will be in the range of microwatts, thus thick antenna metallic layers will not be required. Thicknesses are expected to be in the range of 5 to 10 nm. Recent developments in surface etching show promise for the use of multilayer antenna wiring, which will increase antenna surfaces many fold. Switching facilities will facilitate low power, low loss, and CMOS types of serial/parallel switches to achieve extremely low energy loss. Considering the low power required for switching, power requirements are optimized (minimized) through fast switching capabilities. Even separate elements of the same antenna facilities will have incorporated switches for multiple segment switching. This allows optimization of total antenna capacitance and inductivity resulting in transmitting and achieving high quality resonance reception. Cumulatively, this leads to power conservation.

As previously indicated, information is communicated between individual sensor units, between the sensor units and one or more router units and also between a centralized system computer and the routers and the centralized system computer. During a communication cycle, each data package will consist of a preamble, data, and signature. If the package is not designated, it is directed to the centralized system computer. If the centralized system computer does not send confirmation in the established time frame, the centralized system computer will try to transmit the package via nearby sensor units. In this case, the end of the transmitted package will have a designation mark for chain communication. This mark will trigger any nearby sensor units to receive the package, and immediately retransmit with the same designation mark. In this way, the centralized system computer will receive the package by multiple paths, from other sensor units, and perhaps many times. After receiving the first package, if no errors are present, the centralized system computer will form and transmit a response package with specific information as to which package has been successfully received. This will interrupt all other transmissions of the same package. All units will then switch to the normal operating mode.

For long-range communication each sensor unit can communicate with any and all sensor units. During initial handshake procedures, the sensor units are synchronized and are capable of generating and transmitting data packages simultaneously, forming phase antenna fields on the carrier frequency. During the transmission process, while data is being acquired by one sensor unit, all sensor units from the group will be involved. Before transmission, all members of the group will be assigned unique group numbers. After transmission, the first unit of the group will form a package of data, consisting of preamble, data, and signature. Then, each sensor unit provides package encryption and adds a designation descriptor. The sensor chip transmits these packages to other sensor chips. When another sensor unit(s) receives a package with a destination mark, the mark will be analyzed. If the destination mark prescribes a data package to be transmitted via the long-range communication mode, each sensor unit from the group will receive and place the data package in a special holding queue. All group members then start the RF synchronization cycle and when synchronization is achieved; all group members will transmit one single data package simultaneously, thus increasing the communication distance. After initial data from one of the units is transmitted, the second unit of the group will transmit their own package with a designation signature to all group members and the cycle will then repeat, until all data from all group members has been successfully transmitted. The main receiving unit will form and transmit a confirmation receipt for each package transmitted by the group. If any errors are acquired, the package will be retransmitted a reasonable number of times until error free transmission is achieved.

The power facilities are distributed over and among different circuits. They include antenna facilities; receive, with all distributed amplification; RF processor; power management facilities; and power storage devices.

Each sensor unit has a unique input/output channel for initial power-up, charging the main storage capacitor, programming, and performing test procedures, some of which are activated through a power recovery and storage unit 212. Connection to this port will be accomplished during initial test procedures. During normal operation, meaning operation in an open environment, the sensor unit will not be connected to any external power source for charging and operations. For power acquisition, the sensor unit collects power from the environment, including, but not limited to a solar battery 218. The sensor unit is designed specifically to allow optimal use of unit volume and all system properties for acquisition, storage, and power management. The main power source is the electromagnetic radiation available in the complete radio frequency range received by RF receiver 216. This type of energy is widely available in all places where there is human activity. These sources include radio transmitters in all AM/FM bands; radio receivers, because their converter circuits generate RF waves; police radar-based speed detectors; military or civilian radar; computer monitors, which are a significant near-field RF source; computer networks; and wires within the power grid. Secondary sources of energy are also available and each unit has designated facilities to acquire that energy. Mainly there are X-ray band and Gamma band sources as shown by receiver 220, which are widely available in medical facilities screening facilities in airports, railroad and train stations, etc. Another source of repeatable energy may be motion of the object or surface upon which the unit is installed. An ultrasonic receiver 214 such as a piezoelectric genomic element, will absorb this type of energy. Scenarios locating the unit on a surgical glove or surgical dressing could incorporate these ultrasonic receivers capable of absorbing temperature gradients and producing other health status parameters.

The RF band will be used as following: Power acquisition begins with the idle cycle of the main DSP processor. The DSP will advise the RF processor to open all receiving circuits and start to acquire signals in the wide spectrum. The RF processor will search the complete frequency range and attempt to determine the available energy. If any is available, all input circuits will be optimized on that specific frequency range. Detection and storage of the energy is done by multiple stages of detection and charging of the main capacitors. An optical sensor is the ideal because it collects any energy in the optical or close range bands. This additional function will not degrade main sensor functionality. Energy collected in the x-ray and Gamma-ray bands will be used on the reverse side of the unit. The chip volume in this scenario works like a massive filter of optical rays, allowing detection of only x-ray or Gamma rays. These rays freely penetrate silicone substances. An additional benefit of such a detector and power acquisition element is that the sensor unit will collect information about radiation background and/or radiation bursts.

The main storage capacitors are located on the lower layer of the sensor unit. The capacitors are configured in large fields of non-electrolyte, dry capacitors.

Power management facilities incorporate on/off and hibernation functionality. These circuits are principally designed for monitoring the main load circuits, stages of power consumption, and facilitating a power consumption prediction algorithm. Together with the main software on the DSP, power management software modules will detect the shortfalls of stored power and will re-allocate depending on power cycles. This allows decreased peak consumption and power-related heat consumption. Additionally, the power management unit allows determination of maximum power storage peaks and allocates the maximum consumption at that specific moment, to maximize output transmitting performance. Information about power status is included in each block of data, and in this way the main unit can determine when it needs to run the main charging cycle to restore (replenish) power.

In the case of a new sensor unit or a sensor unit which has totally lost power, all circuits are designed such that receiving circuits switch to maximum power and the power storage cycle is active. In this way, if an operator or the main unit initiates unit activation, they are ready to acquire energy and recharge their power facilities. The replenishment cycle will be postponed until all capacitors are fully charged, and power management facilities will then initiate first wake-up procedures. During wake-up procedures, the DSP runs a simple self-test and then performs a testing of peripheral elements. After the test is successful, the DSP will initiate a short transmission session to check the RF channel. After all this is complete, a status code will be recorded in the memory along with the date and time. If the wake-up status is allowed, the DSP will switch to the normal acquisition and analysis phase. If the wake-up procedures generate a different code, that code will be sent to the main unit for further analysis and subsequent operational instructions. To enhance energy saving during the normal functioning modes, the power management system will power-up only those sensors and systems, needed at that particular moment. In the mode "collect or wait for an event", most of the system is in the power-saving mode. If some facilities are damaged during transportation or from improper previous usage, all possible codes will be stored in the unit memory for detailed scanning. Scanning can be performed with an external device to determine overall power status.

Power conservation is explicitly integrated in the operational power system. All circuits in the sensor unit allow power management in a multiple stage conservation process. The circuits of the sensor units will be monitored for excessive power consumption. If this happens, a status flag of excessive power consumption will be generated and the centralized computer will further analyze that event.

The low power consumption stage is mainly designed to switch non-critical processes to low power, which will make execution time longer, but will provide enhanced power.

A super low power consumption stage will be activated when absolutely non-critical scenarios are encountered. The performance cycles will switch to the minimum possible operating level for very slow continuous operations, with minimum operations needed for survival of the chip, but not crucial for that specific environment. An example of such an event could be long-term survival, when no RF power sources are available, but there is a need to maintain operations to acquire possible energy bursts.

Hibernation of all circuits is not related to power conservation but will reduce the amount of consumed power. Usually hibernation is predictable, controllable, and will often be used during normal operation.

Each of the sensor units will be in the power-off stage when delivered from the factory. There is insufficient power to initiate operational and initialization tests. during this stage all power facilities are oriented to collect and conserve power. No calculations or transmissions are executed.

Figure 12:
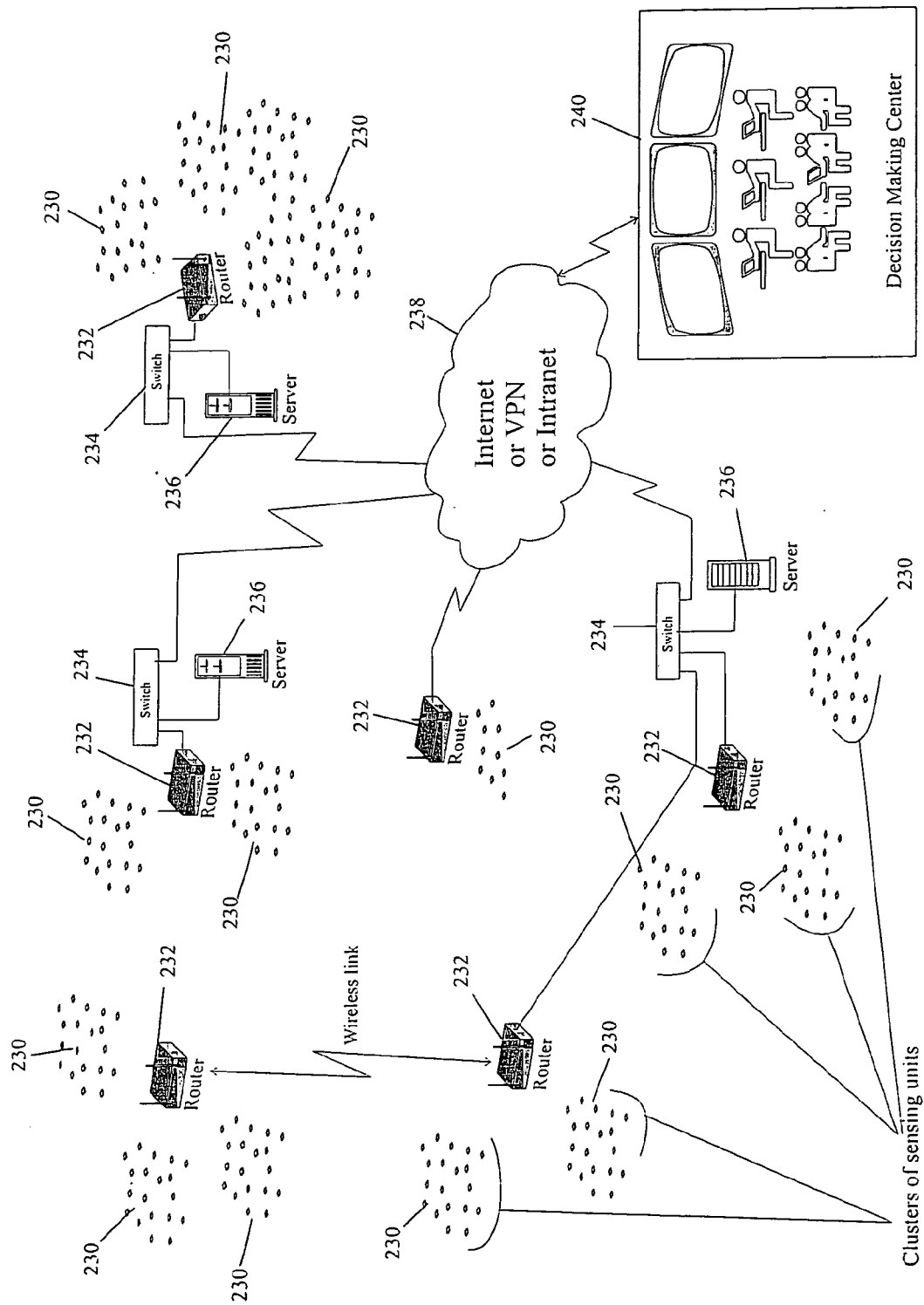

FIG. 12 illustrates the system of the present invention in which a plurality of groups of sensor units 230 are dispersed in various locations. As previously indicated, each of the sensor units within each group 230 can transmit and receive information from any of the sensor units within that group. Each of the sensor units within each of the sensor groups or clusters 230 would also be in communication with a router 232. This communication is generally wireless in nature and would utilize the three types of transmitting technologies previously described. Some of the routers are provided with a switch 234 and a server 236 for transmitting information wirelessly or through an internet, VPN or internet system 238 to a centralized computer system 240. This centralized computer system would receive and transmit data to and from the routers, as well as the individual sensor units. Based upon the information received by the centralized computer system 240, a decision is made as to whether toxic biological substances are prevalent in one or more areas as well as whether this would constitute a bio terrorist attack. This decision making process is done either automatically utilizing an appropriate computer, or in conjunction with individuals reviewing the output of the centralized computer based upon information received from the groups of sensor units 230.

The real time detection of biological substances, to include pathogens, allergens, and microorganisms in multiple diverse environments requires the integration of several scientific bodies of knowledge. As described, the present invention incorporates multiple technologies, demonstrates multiple functions, and has multiple applications.

The multiple technologies include micro miniature integrated circuitry with embedded sensing technologies that capitalize on the uniquely defining characteristics of the biological substances at hand. These characteristics include biochemical, electrochemical, physical, or thermodynamic phenomenon. To enhance the sensitivity, nanotubes are grown in some units as an adjunct to electrodes upon which rest the ligands associated with the selected biological substances. After detection and discrimination, an alert is passed via the integrated circuitry to external receiving devices enabling a digitized alert of the biological substances' presence.

The units are multifunctional. Their functions include: detection, discrimination, amplification, digitizing, filtering, discrimination, energy acquisition from the environment, communication between units and to external routers and controllers, and network based sharing of information. This multiple functionality is possible because state-of-the-art biochemistry, information technology, and integrated circuitry are combined in such a way as to build a synergistic system oriented to the defining characteristics of the biological substances.

As can be appreciated, the individual sensor units and groups of sensor units can be utilized in many different types of environments and can be affixed to many different types of objects. These environments and objects could include their use in blood transfusion operations and blood plasma collection and storage operations as well as being employed with syringe needles. The sensor units could be attached to various types of gloves, such as used in surgery and drawing blood made from rubber and rubber substitutes. Similarly, condoms constructed from rubber and rubber substitutes and other pregnancy prevention devices could also have sensor units being attached thereto.

Various objects provided in a patient's room affixed to bedside point-of-care diagnostics, intensive care locations and hallways could also be utilized as a base for the individual sensor units. Furthermore, various HVAC ventilation systems and equipment could be provided with a plurality of sensor units as well as sensor unit groups. This would also include air moving equipment as well as local air filtration equipment, patient clothing and dressings, bed services, benches and other furniture as well as face masks used by clinicians and patients. Furthermore, the present invention could be employed in toilet facilities for real time urine and excrement analysis or applied to the service or inside of dental and other human prosthetic fixtures. Furthermore, the present invention could be utilized in the animal or pet as well as fish environment.

The present invention has application in the food handling industry to include services of food processing equipment, conveyors, processing rooms, containers, silverware and other equipment including the inside surfaces of cans and containers, storage facilities and transportation equipment. The present invention has application in all aspects of the food chain, such as farms, food sources, waste management and packing houses.

The present invention has application in conjunction with organic materials used to manufacture produces such as leather products, cloth products and plastic products.

The present invention further has application in monitoring places in which the population gathers, such as train stations, airports, bus stations, offices, tunnels, bridges, terminals, distribution centers, stadiums, cafeterias, restaurants, bars and governmental facilities. The present invention would have application to be used in tickets, badges or passports or other identification documentation.

The present invention would also have application with units used in cabins of airplanes, train carriages, water craft, hovercraft, cars, trucks, and similar types of conveyances.

Given this disclosure, alternative equivalent embodiments as well as other uses will become apparent to those skilled in the art. These embodiments and further uses are also within the contemplation of the invention.

What is claimed is:

1. A system for determining the existence of toxic biological substances, comprising:
   a. a plurality of sensor units, each sensor unit further comprising:
      i. a first ligand, oriented to provide optimal sensing capability;
      ii. a first electrostatic pulse signature signal being generated by an interaction occurring when the first ligand binds to at least one first toxic biological target;
      iii. an electrostatic sensing surface, positioned in proximity to the first ligand for detecting the first electrostatic pulse signature signal being generated;
      iv. a measurement means for measuring the detected first electrostatic pulse signature signal provided in proximity with the sensing surface;
      v. a processor provided with a memory having a plurality of stored electrostatic pulse signature signals controlling the operation of each of the sensor units;
      vi. a comparison device connected between the measurement means and the processor for comparing the electrostatic pulse signature signal measured by the measurement means with the stored electrostatic pulse signature signals and generating comparison information;
      vii. an antenna for transmitting and receiving the comparison information; and
   b. a centralized station for controlling the operation of the plurality of sensor units, the centralized station including a central processor, a central memory and an antenna for transmitting and receiving comparison information from the plurality of sensor units, the central station generating an alert based upon the comparison information received from said plurality of sensor units.

2. The system in accordance with claim 1, wherein the alert is generated based upon the number and type of toxic biological substances sensed by the plurality of sensor units.

3. The system in accordance with claim 1, further comprising a router unit used to transmit information received from the plurality of sensor units to the centralized station, as well as to transmit information to the plurality of sensor units.

4. The system in accordance with claim 2, further comprising a router unit used to transmit information received from the plurality of sensor units to the centralized station, as well as to transmit information to said the plurality of sensor units.

5. The system in accordance with claim 3, wherein each of the plurality of sensor units transmits and receives data directly from one or more of the plurality of sensor units.

6. The system in accordance with claim 4, wherein each of the plurality of sensor units transmits and receives data directly from one or more of the plurality of sensor units.

7. The system in accordance with claim 1, further comprising:
   a plurality of ligands, each of the ligands including a ligand sensing surface and ligand orienting surface opposite the ligand sensing surface;
   the ligand sensing surface of the first ligand of the plurality of ligands completely binds with only the first biological target to produce the first electric pulse signature signal; and
   the ligand sensing surface of a second ligand of a plurality of ligands completely binds with only a second biological target to produce a second electric pulse signature signal.

8. The system in accordance with claim 1, wherein the first ligand binds only with the first biological target wherein the interaction between the first ligand and the first biological target produces a first electrostatic pulse signature signal.

9. The system in accordance with claim 1, wherein the measurement means is a field effect transistor (FET) provided with a source region, a gate region and a drain region.

10. The system in accordance with claim 8, wherein the measurement means is a field effect transistor (FET) provided with a source region, a gate region and a drain region.

11. The system in accordance with claim 9, wherein the FET is an electron sensitive field effect transistor (ESFET).

12. The system in accordance with claim 8, further comprising a biological amplification unit connected to the first ligand.

13. The system in accordance with claim 10, further comprising the first ligand of a plurality of ligands, each of the plurality of ligands including a ligand sensing surface and at least one orienting surface, said orienting surface of at least a portion of the plurality of ligands provided in proximity to the gate region of the FET.

14. The system in accordance with claim 9, further comprising a plurality of ligands provided in proximity to the measurement means.

15. The system in accordance with claim 13, wherein the ligand sensing surface of the first ligand of the plurality of ligands completely binds with only the first biological target to produce a first electric pulse signature signal and the ligand sensing surface of a second ligand of a plurality of ligands completely binds with only a second biological target to produce a second electric pulse signature signal.

16. The system in accordance with claim 13, further comprising a gel enveloping at least a portion of the plurality of ligands in proximity with the gate region of the FET.

17. The system in accordance with claim 16, further comprising a plurality of ligands, each of the ligands including a ligand sensing surface and a ligand orienting surface opposite the ligand sensing surface, and a plurality of nanotubes provided between a first electrode and a second electrode, wherein the ligand orienting surfaces of the ligands attach to one of the nanotubes.

18. The system in accordance with claim 17, wherein the ligand sensing surface of the first ligand of the plurality of ligands completely binds with only a first biological target to produce a first electrostatic pulse signature signal and the ligand sensing surface of a second ligand of the plurality of ligands completely binds with only a second biological target to produce a second electrostatic pulse signature signal.

19. The system in accordance with claim 17, further comprising a catalyst provided on the gate region.

20. The system in accordance with claim 18, further comprising a catalyst provided on the gate region.

21. The system in accordance with claim 17, further comprising conductive or semi-conductive materials coating the surface of the plurality of nanotubes.

22. The system in accordance with claim 18, further comprising conductive or semi-conductive materials coating the surface of the plurality of nanotubes.

23. The system in accordance with claim 1, further comprising a biological amplification unit connected to the first ligand.

24. The system in accordance with claim 1, wherein the processor records and stores a match between the electric pulse signature signal measured by the measurement means and one of the stored electric pulse signature signals.

25. The system in accordance with claim 1, further comprising a device for collecting energy from the optical spectrum, the energy used to power the sensor unit.

26. The system in accordance with claim 1, further comprising a device for collecting energy from the X-ray and gamma ray spectrum, the energy used to power the sensor unit.

27. The system in accordance with claim 1, further comprising a device for collecting energy from an electromagnetic RF field, the energy used to power the sensor unit.

28. The system in accordance with claim 1, further comprising:
   the first ligand of a plurality of ligands, each of the first ligand of the plurality of ligands including a first ligand sensing surface and at least one first ligand orienting surface; and
   a second ligand of a plurality of ligands, each of the second ligand of the plurality of ligands including a second ligand sensing surface and at least one second ligand orienting surface, the first and second orienting surfaces of at least a portion of the plurality of ligands provided in proximity to the measurement means.

29. The system according to claim 28 wherein the orienting surface of the first ligand of the plurality of ligands is placed in proximity to the electrostatic sensing surface by a coating applied to the electrostatic sensing surface and a cross-linker that links the orienting surface of the first ligand of the plurality of ligands to the electrostatic sensing surface.

30. The system according to claim 28 wherein the first and second orienting surfaces of the first and second ligand of the plurality of ligands s are placed in proximity to the electrostatic sensing surface by a coating applied to the electrostatic sensing surface and a cross-linker that links the first and second orienting surfaces of the first and second ligand of the plurality of ligands to the electrostatic sensing surface.

31. The system according to claim 28 wherein the orienting surface the first ligand of the plurality of ligands is placed in proximity to the electrostatic sensing surface by using an electrostatic field.

32. The system according to claim 28 wherein the first and second orienting surfaces of the first and second ligand of the plurality of ligands are placed in proximity to the electrostatic sensing surface by using an electrostatic field.

33. The system in accordance with claim 1, further comprising nanotubes utilized to increase a surface area of the electrostatic sensing surface to increase sensing capability for biological target detection.

34. The system in accordance with claim 1 wherein the processor records and stores a match between the first electrostatic pulse signature signal measured by the measurement means and the stored electrostatic pulse signature signals.

35. A system according to claim 1 further comprising:
   a) a chemical coating applied to the electrostatic sensing surface; and
   b) the first ligand is oriented and tethered to the chemical coating by a cross linker to provide the optimal sensing capability.

* * * * *